United States Patent [19]
Scalise et al.

[11] Patent Number: 5,812,678
[45] Date of Patent: Sep. 22, 1998

[54] AUSCULTATION AUGMENTATION DEVICE

[76] Inventors: Stanley J. Scalise, Palm Beach Gardens, Fla.; Adele Scalise Rainone, 4584 Satinleaf La., Sarasota, Fla. 34241, legal representative of said Stanley J. Scalise, deceased; Dennis W. Davis, 10740 Eland St., Boca Raton, Fla. 33428

[21] Appl. No.: 606,567

[22] Filed: Feb. 26, 1996

[51] Int. Cl.⁶ .................................................. A61B 7/04
[52] U.S. Cl. ........................ 381/67; 381/71.6; 381/71.7
[58] Field of Search ...................... 381/67, 71.6, 71.7; 128/715

[56] References Cited

U.S. PATENT DOCUMENTS

| | | | |
|---|---|---|---|
| 4,248,241 | 2/1981 | Tacchi | 128/671 |
| 4,845,751 | 7/1989 | Schwab | 381/25 |
| 4,847,903 | 7/1989 | Schotz | 381/3 |
| 4,981,139 | 1/1991 | Pfohl | 128/671 |
| 5,375,174 | 12/1994 | Denenberg | 381/71.6 |
| 5,492,129 | 2/1996 | Greenberger | 128/715 |
| 5,539,705 | 7/1996 | Akerman et al. | 367/132 |
| 5,539,831 | 7/1996 | Harley | 381/67 |
| 5,550,902 | 8/1996 | Abbruscato | 379/106 |

*Primary Examiner*—Forester W. Isen

[57] ABSTRACT

A noise-canceling biological sound monitoring system provides electronic noise cancellation at the pickup head by using a primary transducer to sense anatomy sounds and a secondary sensor as a noise monitor. The system philosophy emphasizes the capability to provide the medical practitioner with an improved signal-to-noise ratio while at the same time maintaining the character of the sound to which the practitioner is accustomed. Various embodiments of the system include a device for use as an amplifying aid with conventional stethoscopes and a system which provides telemetry of sound to a remote receiver for listening, analysis or recording.

26 Claims, 18 Drawing Sheets

AUSCULTATION AUGMENTATION DEVICE

BACKGROUND

1. Field of the Invention

This invention relates to stethoscopes in general and in particular to stethoscope aids including electronic amplification circuitry. More specifically, this invention relates to improved electronic stethoscope aids having robust noise cancellation and high fidelity signal amplification.

2. Description of the Prior Art

During the course of using a stethoscope, medical personnel are often faced with difficulty in hearing the heart and breathing sounds of a patient. In particularly noisy environments, with elderly and obese patients, and in the case of a somewhat hearing impaired medical person, the need arises for a means of suitably amplifying body sounds presented to a normal stethoscope in as unobtrusive a manner as possible.

For many emergency scenarios, a physician's stethoscope is the first diagnostic device used in determination of the patient's immediate condition. Often it is the only device used prior to initiation of immediate first treatment. It is often very difficult to hear with sufficient clarity the vital breathing and heart sounds of a medically distraught individual. Additionally, health care personnel such as paramedics and triage unit members working in high ambient noise environments could benefit greatly from a device that amplifies the conventional stethoscope sound signal. Similarly, veterinarians could benefit as well when using the device in the field.

Electronic stethoscopes have been introduced to address some of the aforementioned problems. However, since many health care professionals are reluctant to relinquish the use of the stethoscope that they have relied upon since their earliest medical training, cost-effective augmenting means that improve the performance of conventional stethoscopes can find ready acceptance. Hence, the basic embodiment of the presently disclosed invention consists of a compact device that is placed between the patient's anatomy and the conventional stethoscope. Noise cancellation and signal amplification are achieved within this device at the location closest to the source of desired sound. Embodiments of the device also provide a telemetry capability. The purpose of the system described in this disclosure is to significantly enhance the performance of a conventional stethoscope by providing an effective means of faithfully amplifying the heart, breathing, and other anatomy sounds of the patient while diminishing noise.

Subject matter of pertinence to the presently disclosed invention includes electronic stethoscopes, amplified conventional stethoscopes, noise cancellation, hearing aids, and telemetry techniques.

Prior art contains various versions of the electronic stethoscope. One main approach to implementation of an electronic stethoscope involves the electronic amplification of sound acoustically delivered to a microphone from a conventional stethoscope sensing head. U.S. Pat. No. 3,247,324 to Cefaly, et. al. discloses a conventional pickup head acoustically coupled by flexible conduit to a microphone-amplifier-speaker assembly that is then acoustically coupled to a conventional binaural headpiece. The electronic stethoscope disclosed in U.S. Pat. No. 3,247,324 also permits direct acoustic connection between the pickup and the binaural headpiece. U.S. Pat. No. 4,528,690 to Sedgwick details a similar amplifier scheme similar to that of Cefaly, et. al., but with the addition of a battery saving circuit and U.S. Pat. No. 4,618,986 to Hower provides the additional features of a battery timer, a folding storage geometry, and pacing interval tones for pulse rate measurement. The second main approach found in prior art makes use of a microphone or electronic-acoustic transducer as the pickup head rather than a conventional pickup head. U.S. Pat. No. 3,160,708 to Andries, et. al. discloses a stethoscope pickup head that comprises a cone-shaped acoustic horn that feeds the signal to a microphone diaphragm. U.S. Pat. No. 4,072,822 to Yamada provides a pickup head that operates in either of two modes, as a conventional acoustic stethoscope or as a microphone sensor that is amplified and connected to speakers contained in the earphones. U.S. Pat. No. 4,071,694 to Pfeiffer is also a stethoscope that has the capability to operate as a conventional stethoscope or as an electronic stethoscope, but that includes volume control and frequency selection. An amplification device for conventional stethoscopes is disclosed in U.S. Pat. No. 4,048,444 to Giampapa. In this patent, microphone-amplifier-speaker assembly devices are attachable to each of the two earpieces of a conventional stethoscope headpiece. Critical to the acceptance of electronic stethoscopes by the medical community is the requirement that they provide an acoustic response that mimics the conventional stethoscope with that medical personnel have gained much of their diagnostic experience. Prior art has failed to adequately address this issue.

A noise-canceling stethoscope is embodied in U.S. Pat. No. 4,438,772 to Slavin. In this invention, the acoustic signals from two separate conventional stethoscope pickup heads (one sensing both desired and undesired signal, and the other sensing preferentially the undesired signal) are acoustically conducted to an electronic unit. The electronic unit uses microphones to detect these acoustic signals. The electronic unit then performs the electronic differencing of these signals and amplification of the resulting difference signal. The amplified difference signal drives a speaker for acoustic conduction to a conventional stethoscope headpiece.

Because the noise energy enters an acoustic sensing system from numerous directions in both radiative and conductive fashions, the sensed ambient noise field is diffusely distributed. Darlington, et. al., showed, by using a primary and a reference sensor separated by just a few centimeters in a diffuse noise field, that the coherence between corresponding sensor signals is very small at frequencies greater than 1 kilohertz, and increases with decreasing frequency. The implications of this field diffusivity are pivotal to the design of efficacious noise-canceling systems. In a preferred embodiment of the present invention, coherence is maintained between the noise detected on the signal channel and noise detected on the reference channel within a compact sensor head. This allows achievement of high signal-to-noise ratios when the respective channel inputs are differenced.

A number of prior art citations deal with the telemetry of stethoscope signals for remote listening, analysis and recording. U.S. Pat. No. 3,989,895 to O'Daniel discloses a stethoscope having means for simultaneous conventional acoustic output to a listener and electronic output of the signal for recording. U.S. Pat. No. 4,248,241 to Tacchi provides for the radio frequency telemetry of patient biological sounds to a portable receiver worn by an anesthesiologist. U.S. Pat. No. 4,705,048 to Pfohl provides infrared telemetry of sound data for the same purpose as the patent to Tacchi. These techniques invoke alterations of the fundamental stethoscope and therefore do not telemeter sound characteristic of the unaltered stethoscope. Furthermore, the use of robust noise cancellation techniques in the sensor head is not disclosed.

Another area of prior art that is pertinent to the present invention is that of noise cancellation in hearing aids. U.S. Pat. No. 5,412,735 to Engebretson, et. al. and U.S. Pat. No. 5,402,496 to Soli, et. al., disclose the parallel processing of the single channel audio input to a hearing aid. The input is characterized as containing signal and noise components. In these inventions, the input is processed along a path ancillary to the main path in order to provide an adaptive estimate of the noise component. The estimated noise component is then subtracted from the input present on the main path. In U.S. Pat. No. 5,170,434 to Anderson, an ancillary processing path provides a control for adapting the filtering that takes place on the main processing path. Further sound perception improvement is provided by inventions that provide adaptation with a man-in-the-loop. Examples of this approach include the inventions of U.S. Pat. No. 5,396,560 to Arcos, et. al., and U.S. Pat. No. 5,027,410 to Williamson, et. al., In the former case, novelty filtering emphasizes energy contained in signal spectral bands over the broadband background noise energy. In the latter case, adaptive, programmable filtering allows the hearing aid user to effectively optimize the settings of an equalizer that compensates for physiological hearing loss the user may have in selected frequency bands.

The inventors of the presently disclosed device are not aware of any prior art that teaches a means of improving the quality of the auscultation achievable with a conventional stethoscope by amplification and noise abatement at the location of sound pickup. In addition to providing a conventional stethoscope with improved output sound quality, the present invention is disclosed in a number of embodiments that increase the usefulness of conventional stethoscopes. The present invention is an elaboration on the ideas presented in U.S. Patent and Trademark Office Document Disclosure No. 384,787 filed Nov. 20, 1995.

SUMMARY OF THE INVENTION

The main object of the present invention is to provide a compact, battery-powered device to be used with a conventional stethoscope that will materially improve the signal-to-noise-ratio of the stethoscope output while maintaining the fidelity of sensed anatomy sounds. A basic preferred embodiment of the invention is a small, self-contained sensing head that is placed on the patient and that is then coupled to the bell of a stethoscope. This device incorporates two sound-sensing transducers, one that picks up anatomy sounds and ambient noise, and another that preferentially picks up ambient noise alone. Noise cancellation is effected by the electronic differencing of the amplified outputs of these transducers. The resulting signal drives a microphone that relays the sound to the stethoscope bell in contact with the device. An automatic activation circuit is included that allows minimal current drain when the device is not in use. An elaboration of the basic idea of the invention comprises a modular device that is separable into a sensing portion, and a receiving and annunciating portion. The two portions of the device can be used in locked-together fashion in the same way the basic embodiment is used or the two portions can be separated so that auscultation of a patient can be achieved at some distance from the patient. In the separated mode, the sensing portion in contact with the patient transmits a signal over a modulated carrier to the receiving and annunciating portion that is in contact with the stethoscope. With the use of a number of such receiving and annunciating portions and a corresponding number of stethoscopes, numerous persons can remotely listen to the sounds transmitted by a single sensing portion of the device. An extension of this telemetry idea uses repeaters for transfer of the signal information to remote locations. Listening, recording, or analyzing functions can be conducted at these remote locations. Further, the use of electrical power mains for communicating the sound information throughout the physical extent of a large building or hospital is disclosed. A novel receiver embodiment has provision for recording and playback of sound through the stethoscope.

The following definitions serve to clarify the disclosed and claimed invention:

Anatomy sounds refers to those sounds emanated by the bodies of humans and animals due to biological processes such as respiration, cardiac activity, and digestion, as well as sounds resulting from the articulation of soft and hard tissues.

Conventional stethoscope refers to a stethoscope that is in common use by health care professionals. Such a device comprises a passive pickup head with bell acoustically connected by means of rubber or plastic tubing to the bifurcating junction of a binaural headpiece having rubber earpiece terminations for insertion into the ear canal.

Pressure sensitive transducer refers to any form of device that converts acoustic pressure variation into electrical signals; this includes microphones, and piezoelectric and optical devices.

Coupling means to the stethoscope refers to that part of the geometry of the invention that allows the bell of the stethoscope to couple sound energy into the invention.

Receiving and relaying subsystem is the terminology that refers to various hardware architectures that incorporate either a receiver or repeater that communicates with either audio annunciators (such as speakers or headphones), analysis devices (that include signal processing), video annunciators (such as display terminals), or recording devices (magnetic media or electronic media).

Familiar output sound quality refers to the character of sound to which a person is accustomed when listening to a conventional stethoscope.

Annunciation means generally refers to means whereby the user of the invention can be made aware of the auscultated sounds. Such means include audio annunciators, video annunciators, processors, and recorders. Audio annunciators include hearing devices such as speakers, earphones, and headsets. Video annunciators include cathode ray tubes, liquid crystal displays, or light-emitting diode displays. Processors provide analysis of the received sound signals and can generate visual or hardcopy output. Recording devices such as magnetic tape recorders, floppy disk or hard disk drives, or random access memory systems can provide archiving of the sound information.

Signal analyzing unit refers to a device that processes the received anatomy sounds for the extraction of various types of information useful for medical diagnosis.

Receiving system refers to any device that incorporates a receiver for receiving modulated carrier energy, whether it be acoustic, optical or radio frequency in nature.

Sound transducer refers to a device that converts electrical signals to acoustic signals, such as a speaker.

Enhancement refers to any improvement in the character of an electrical signal by analog or digital signal processing. This includes such improvements as removal of spectral artifacts due to the hardware that detects or transmits the signal.

OBJECTS AND ADVANTAGES

Several objects and advantages of the present invention are:

(a) to provide a system that can be used in concert with a conventional stethoscope, does not alter the stethoscope in any way, and that achieves high fidelity amplification of patient anatomy sounds;

(b) to provide a system that can be used in concert with a conventional stethoscope that achieves robust noise cancellation in even high noise environments;

(c) to provide a system that can be used in concert with a conventional stethoscope that does not impact the character of the anatomy sounds signal sensed by the conventional stethoscope alone;

(d) to provide a system that can be used in concert with a conventional stethoscope that provides the capability of high fidelity telemetry from the patient to remote stethoscopes;

(e) to provide a system that can be used in concert with a conventional stethoscope that is easy to use;

(f) to provide a system that can be used in concert with a conventional stethoscope that is physically compact;

(g) to provide an anatomy sounds monitoring system that provides noise cancellation and telemetry of high fidelity sound data to remote processing and receiving subsystems;

(h) to provide a noise-canceling anatomy sounds monitoring system that provides electronic simulation of the acoustic response of a stethoscope.

BRIEF DESCRIPTION OF THE DRAWINGS

In the drawings, closely related figures have the same number but different alphabetic suffixes.

Figure 9A:
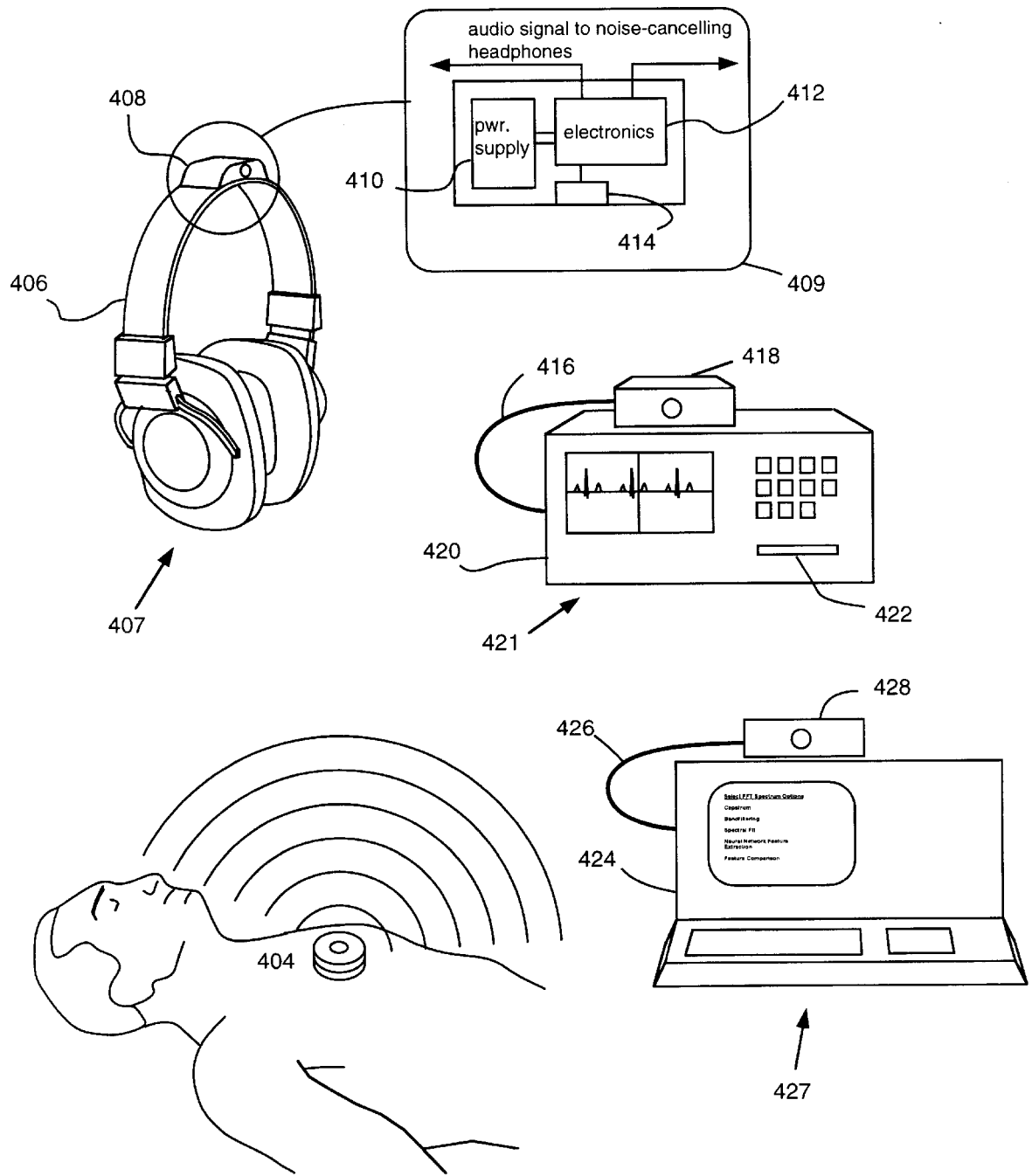
FIG. 9a is a pictorial diagram of the noise-canceling system transmitting to remote receiving subsystems. The subsystem options shown are.
Figure 9B:
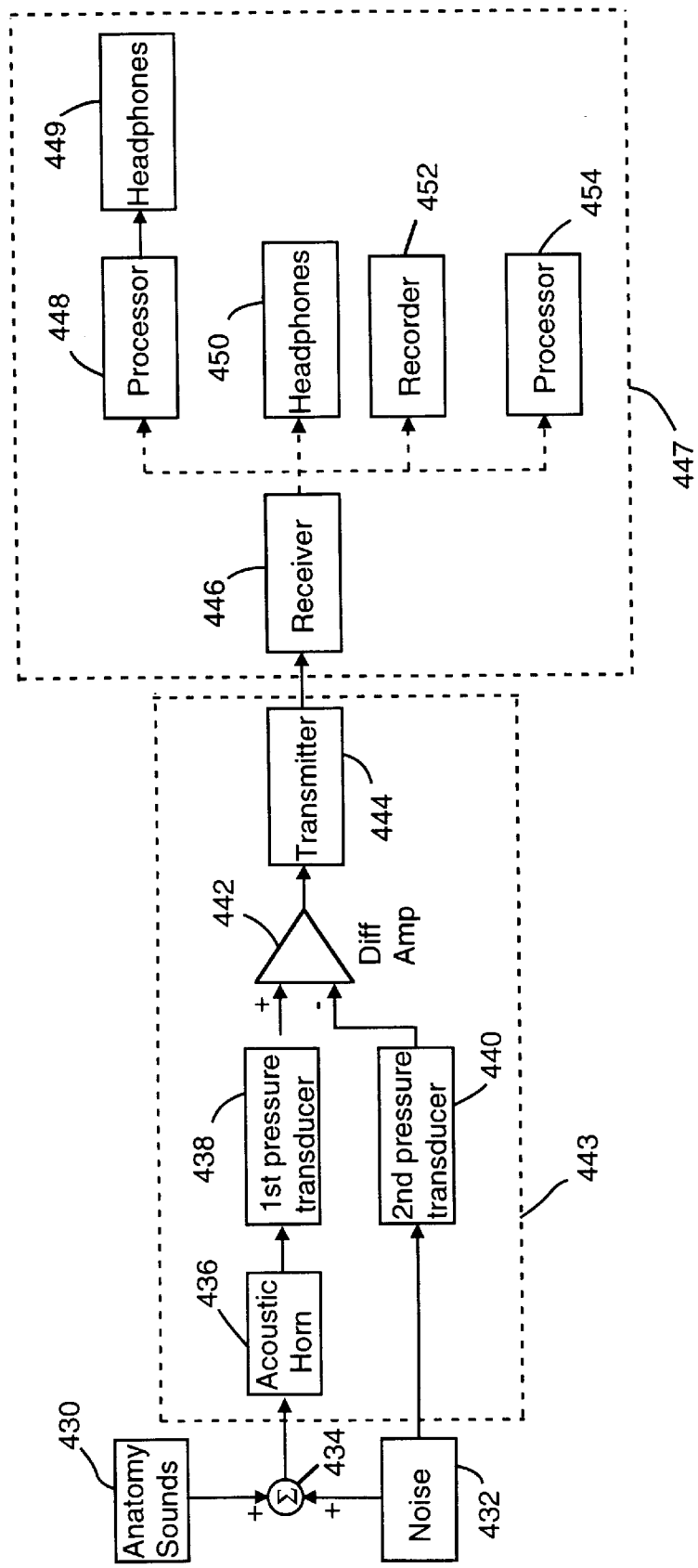
Figure 10A:
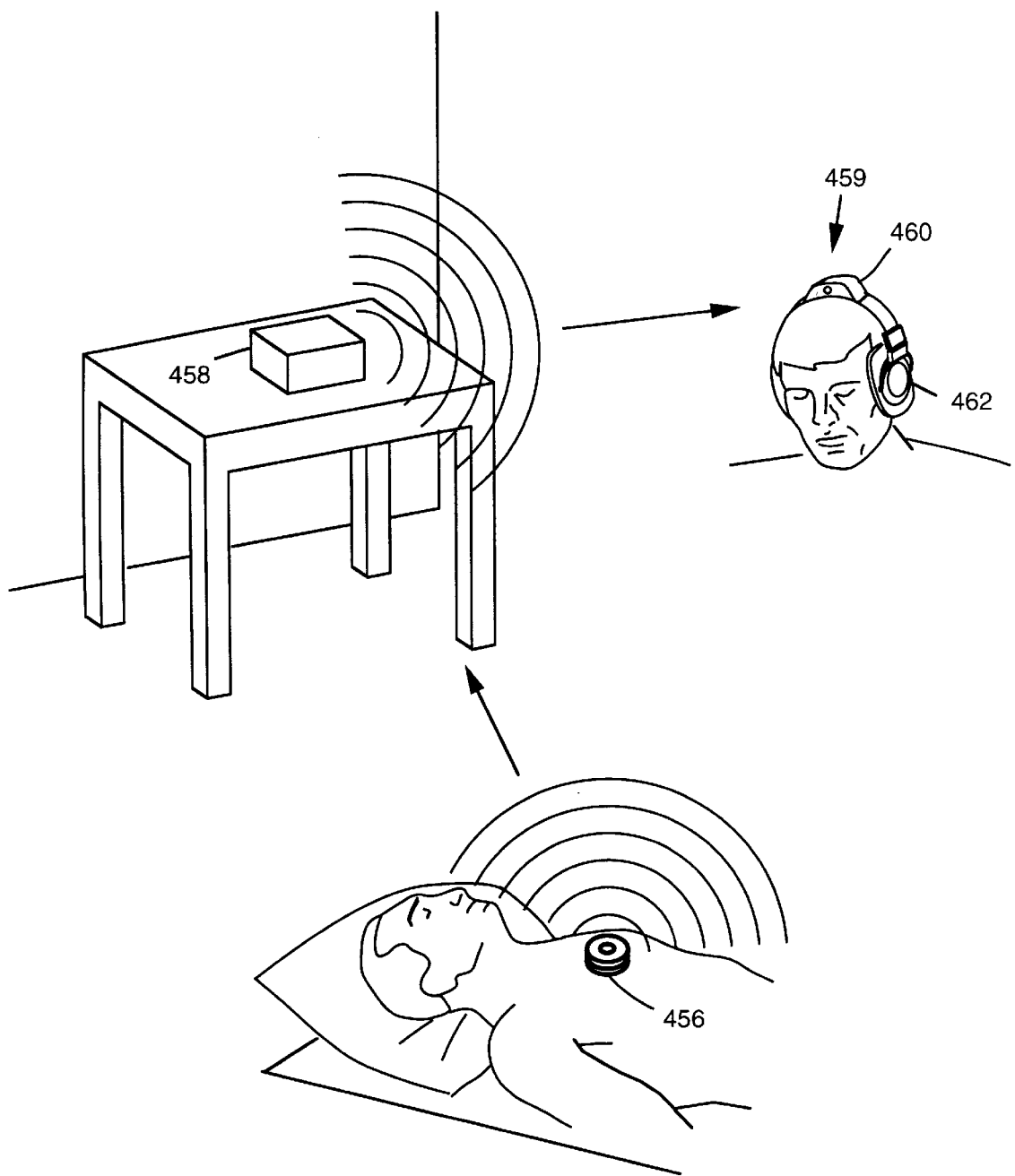
Figure 10B:
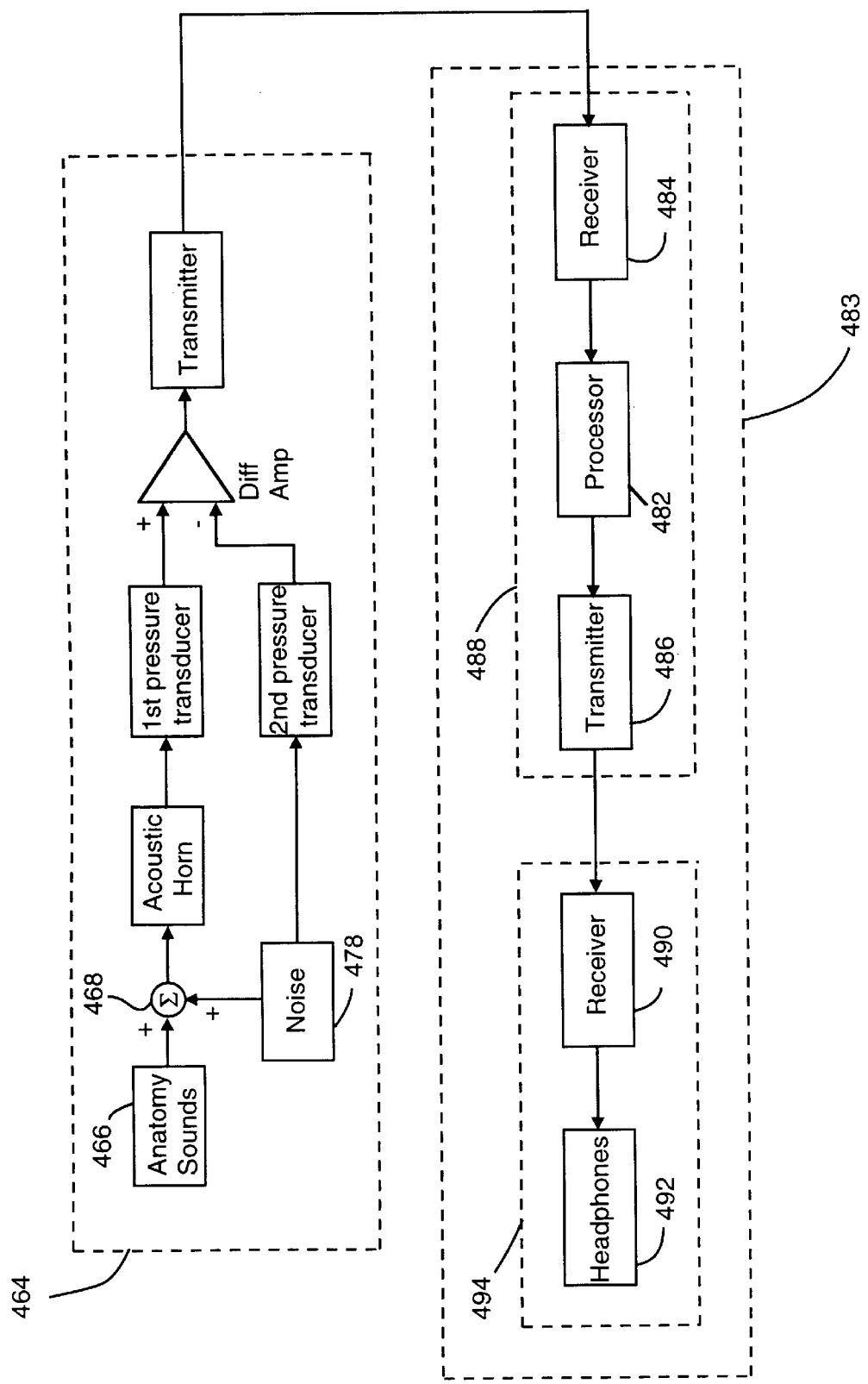
Figure 11:
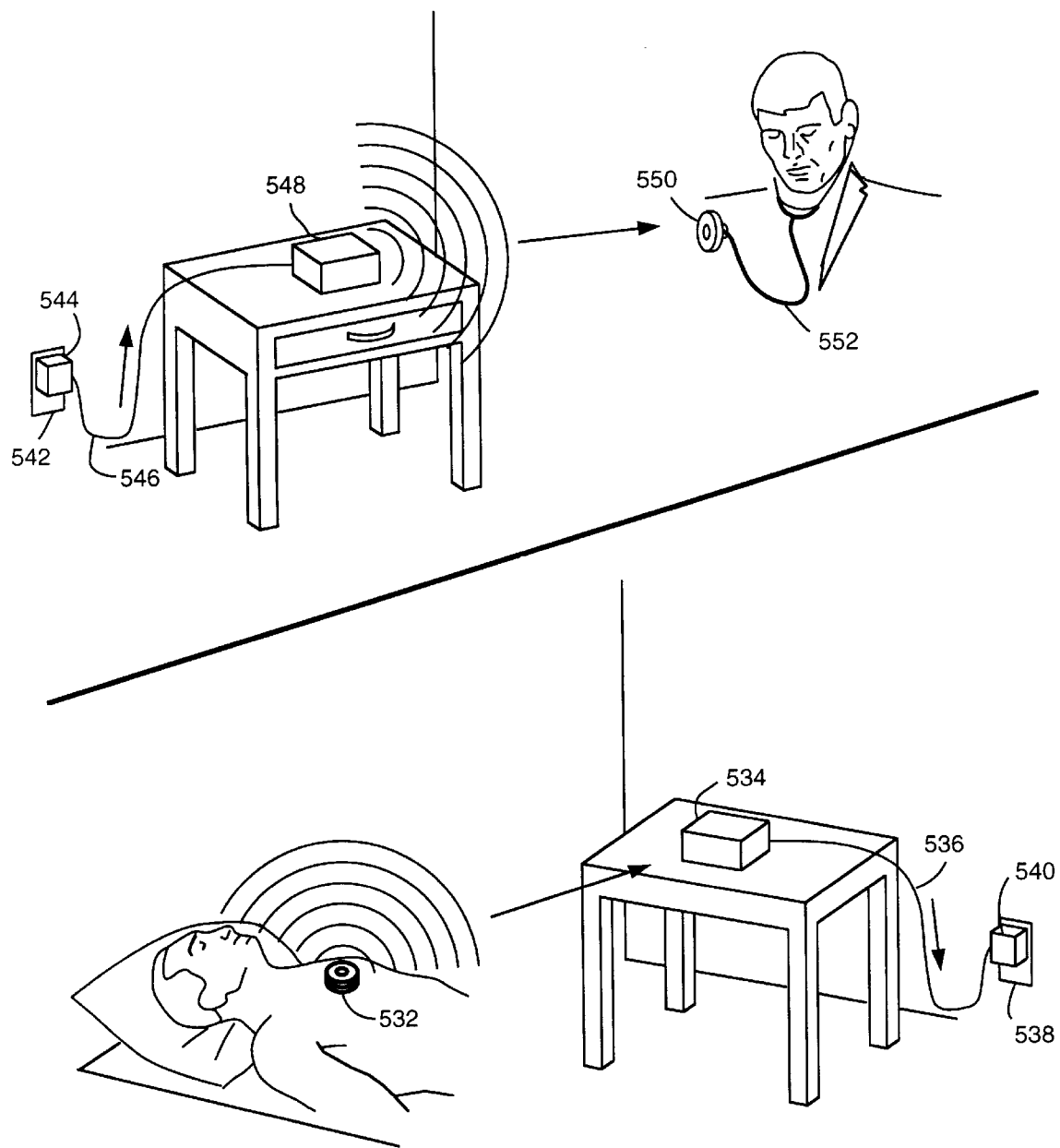
Figure 12:
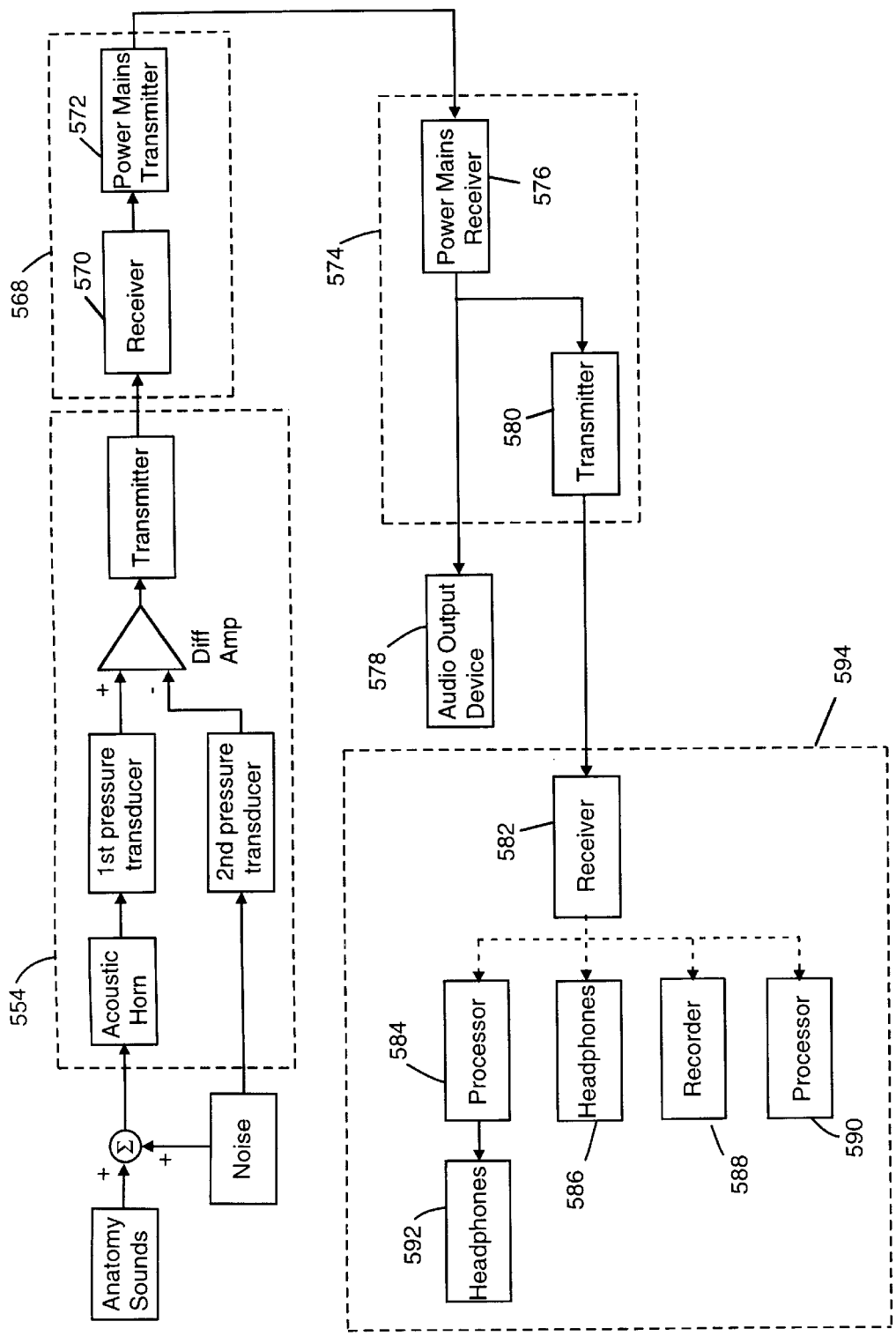
Figure 13:
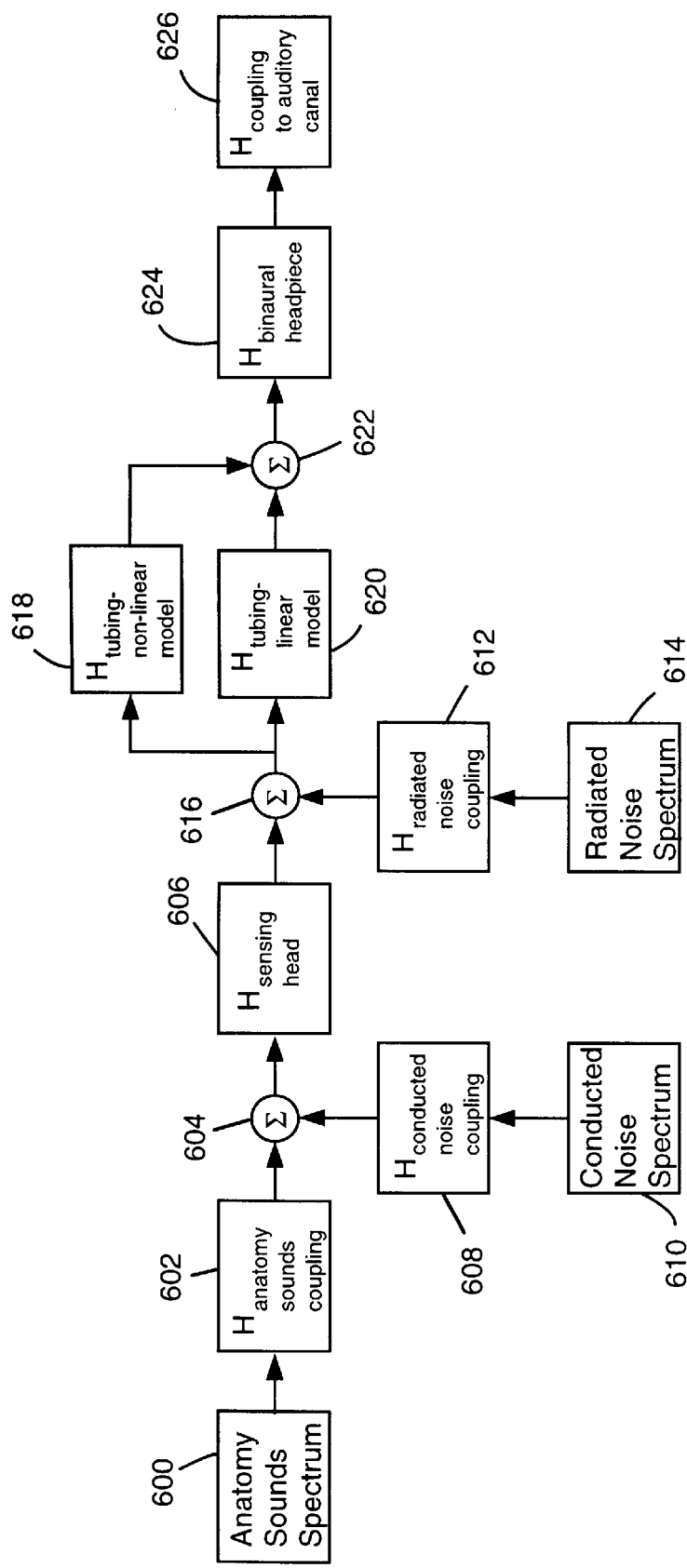
Figure 14:
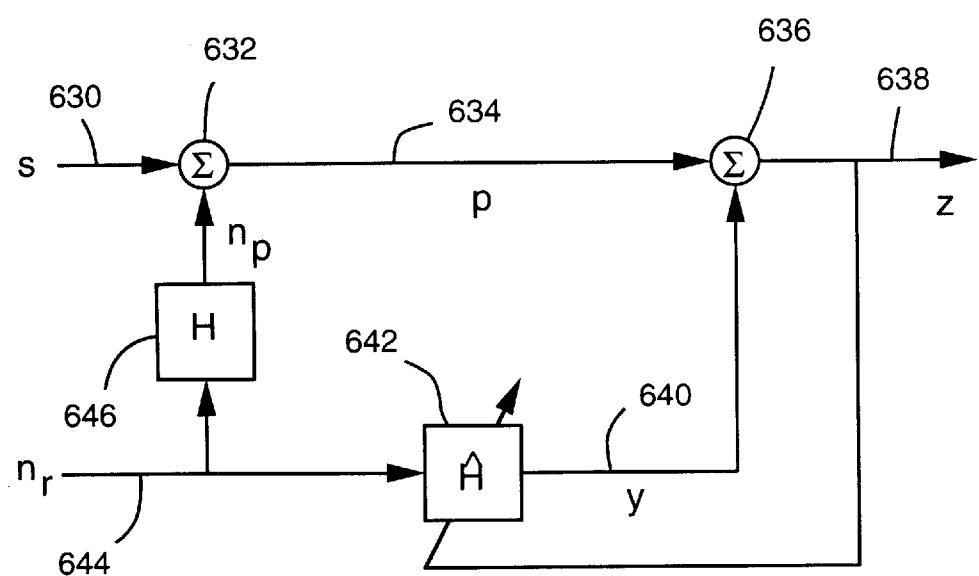

a. audio annunciation device
b. analyzer
c. recorder
d. transceiving processor and audio annunciation device;

FIG. 9b is a functional block diagram of the noise-canceling system that transmits to remote receiving subsystems;

FIG. 10a is a pictorial diagram of embodiments using two stages of transmission;

FIG. 10b is a block diagram of the two stage transmission system;

FIG. 11 is a pictorial diagram of a system using power mains communication;

FIG. 12 is a block diagram of a system using power mains communication;

FIG. 13 is a transfer function block diagram of a conventional stethoscope;

FIG. 14 is functional block diagram of a noise-canceling adaptive filter;

DETAILED DESCRIPTION OF THE INVENTION

The noise-canceling system for use with a conventional stethoscope consists of a compact cylindrically shaped assembly containing a shaped acoustic chamber at one end. The task of the chamber is to efficiently couple the anatomy sounds to a pressure sensitive transducer contained within the assembly. The pressure transducer output is amplified by high gain microelectronics circuitry contained within the body of the assembly. The other end of the assembly is fitted with a pressure transmitter that, when driven by the output of the internally contained microelectronics, creates a faithfully amplified reproduction of the patient's anatomy sounds. A conventional stethoscope is placed against that output end of the assembly in order to facilitate coupling of the amplified sounds to the bell of the regular stethoscope. In this manner, and only when required, the user may augment his or her own stethoscope by placing the stethoscope against the output end of the aid. Most medical personnel prefer to use their own stethoscope, since they are familiar with its feel and performance and carry it around faithfully. This device augments that stethoscope's capability in a compact device that easily fits in a pocket for storage when not in use and that does not physically alter the existing stethoscope during use. It also precludes the need for a separate, often bulky electronic stethoscope with its related storage problems.

An important feature of a preferred embodiment of the present invention is that the assembly not only contains the pressure transducer used to pick up the anatomy sounds, but also includes a second transducer buried in the body of the assembly that is not exposed to the shaped acoustic collection chamber. The first transducer picks up the anatomy sounds and the conducted sounds produced by handling the assembly during use as any significant ambient noise produced by the environment. The second transducer picks up only conducted sounds produced by handling the assembly and any significant ambient noise. The unwanted noises are differentially suppressed by the electronics circuitry within the device. This dramatically reduces the amplified noises due to handling and any significant ambient noise pickup and allows for significant amplification of only the anatomy sounds. These amplified anatomy sounds are easily handled by the user's own stethoscope with excellent signal-to-noise ratio and minimal spectral coloration.

Figure 1A:
FIG. 1a is a pictorial of the basic noise-canceling stethoscope system.

FIG. 1a pictorially illustrates a basic embodiment of the invention, that of a single self contained package for easy use with a conventional stethoscope. One face of the noise-canceling amplifier device 1 is placed in contact with the patient. The other face of the device is placed in contact with the bell 2 of the stethoscope 3. All of the necessary electronics and a battery power source are fully contained within the device 1. The device 1 can be implemented in number of different ways; it can include a single sound transducer with associated noise-canceling electronics, it can include multiple sound transducers for differential sensing of noise, and it can use various sound transducers. The sound transducers can be microphones of various types such as electret, piezoelectric, or magnetic. Fiber optic acoustic sensors that are similar in principle to fiber optic hydrophones (for example U.S. Pat. No. 5,363,342 to Layton, et. al. and associated references) can also be used in the present invention. These induce a path length-integrated effect over the significant path lengths provided by the coils of optical fibers used in the sensor.

Figure 1B:
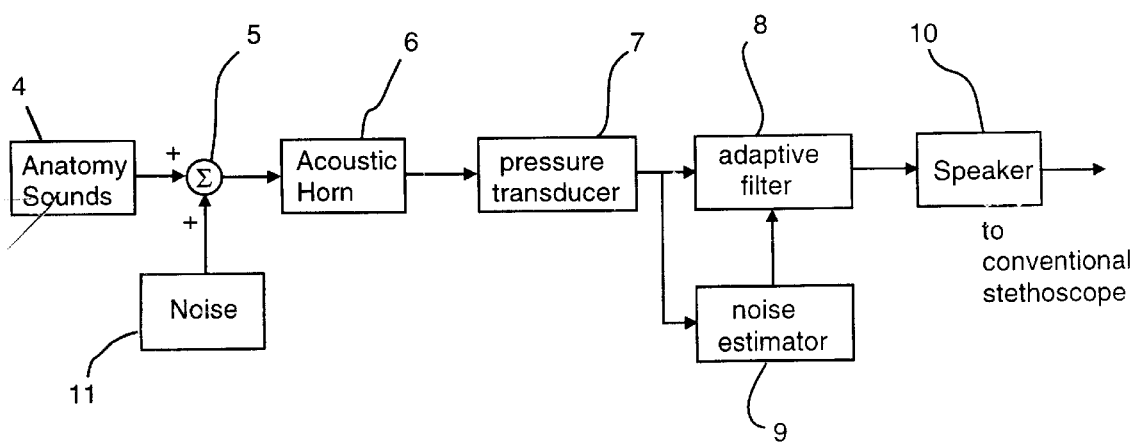
FIG. 1b is a functional block diagram of the single channel noise-canceling stethoscope system that uses adaptive filtering in the main processing path.

FIG. 1b is a functional block diagram of a single transducer, or single channel, version of the device. Both anatomy sounds 4 and noise 11 enter the acoustic horn of the device 6 that is placed in contact with the patient. Anatomy sounds 4 and noise 11 are represented as joint inputs to the acoustic horn 6 by virtue of summing junction 5. The signal plus noise energy is conducted by the acoustic horn to a pickup pressure transducer 7 that converts the acoustic input to an electrical signal. This electrical signal, having both noise and anatomy sound components, is processed by a noise estimator 9 that determines the type and degree of modification to be applied to the signal in the adaptive filter 8. The adaptive filter 8 sustains altered temporal and/or spectral characteristics under the direction of the noise estimator 9 so as to minimize the amount of noise that is passed by the adaptive filter 8. The result of this noisecanceling process is a much improved signal-to-noise ratio representation of the anatomy sounds. The output of the noise-canceling process can be amplified in the adaptive filter 8 as well. The amplified signal is then output to a speaker 10 contained within the device for coupling to the stethoscope.

Figure 1C:
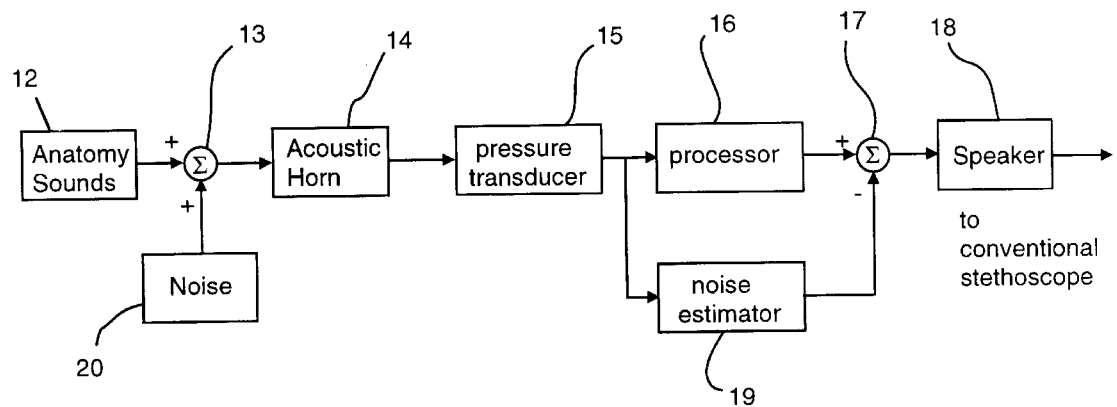
FIG. 1c is a functional block diagram of the single channel noise-canceling stethoscope system that uses noise estimation in the ancillary processing path.

FIG. 1c is a functional block diagram of an alternate single sound transducer embodiment of the device. Again, anatomy sounds 12 and noise 20 are additively coupled at summing junction 13 into the acoustic horn 14 of the device and received by a pressure transducer 15. In this embodiment, the output of the pressure transducer 15 is subjected to parallel processing. One path takes the input through a noise estimator 19 that provides as output an estimate of the actual noise component of the input. The other path takes the input through a processor 16 that can represent the degenerate situation of a simple feed through of the input to the output, or can include amplification and filtering functions. The noise estimate from estimator 19 is subtracted from the output of the processor 16 at summing junction 17 so as to provide a signal largely devoid of noise for input to speaker 18.

Figure 1D:
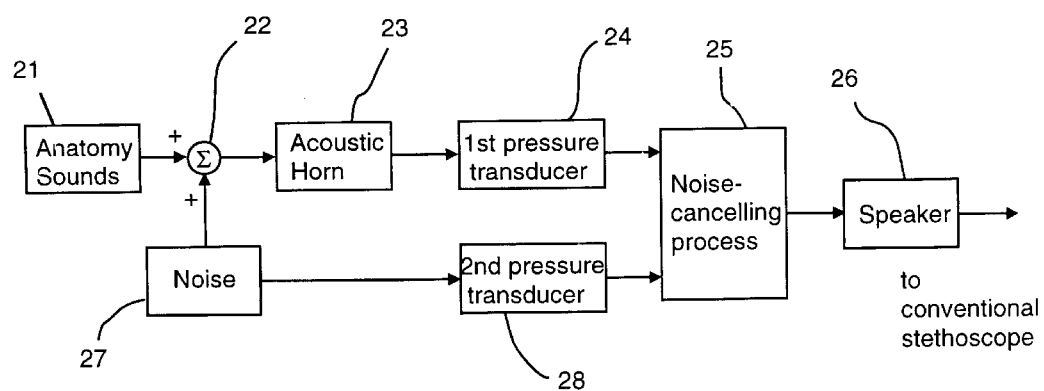
FIG. 1d is a functional block diagram of the two channel noise-canceling stethoscope system.

FIG. 1d is a functional block diagram of a preferred embodiment of the device that uses two pressure sensitive transducers. Both anatomy sounds 21 and noise 27 enter the acoustic horn of the device 23 that is placed in contact with the patient. Anatomy sounds 21 and noise 27 are represented as joint inputs to the acoustic horn 23 by virtue of the summing junction 22. This signal plus noise energy is conducted by the acoustic horn 23 to a first pickup pressure transducer 24. A second pickup pressure transducer 28 in close physical proximity to the first transducer 24 preferentially senses the noise 27. Transducers 24 and 28 convert their respective inputs to electrical signals that are jointly processed in the noise-canceling process block 25. The noise-canceling process can comprise simple electronic differencing of the signals in a differential amplifier or a sophisticated algorithmic process. Candidate algorithmic techniques will be discussed below. The result of the noise-canceling process is a much improved signal-to-noise ratio representation of the anatomy sounds. The output of the noise-canceling process is amplified in block 25 as well. The amplified signal is then output to a speaker 26 contained within the device for coupling to the stethoscope.

Other functional embodiments of the present invention include combinations of the noise canceling techniques of FIGS. 1b and 1c with the dual transducer technique of FIG. 1d. For example, the noise canceling block 25 of FIG. 1d can comprise high fidelity amplification of the first pressure transducer output and separate, adaptive filtering (as depicted in FIG. 1b or 1c) of the second pressure transducer output to further emphasize its noise content. The latter signal can then be subtracted from the former to provide, again, a relatively noise free replica of the sensed anatomy sounds. The present invention includes the use of even more than two transducers in a stethoscope augmenting device as described herein. An array of such transducer outputs can be processed jointly in various ways in order to reduce the noise in the final output of the device.

The use of two transducers allows, by virtue of the physical placement of the transducers, the ability to extract the noise component of the signal without reliance on signal processing means; this favors a dual transducer approach. Further, the simplicity and relatively good performance of a noise-canceling approach that simply subtracts the signal of the second transducer from that of the first transducer in FIG. 1d recommend it as a preferred processing embodiment in the present invention.

Figure 2:
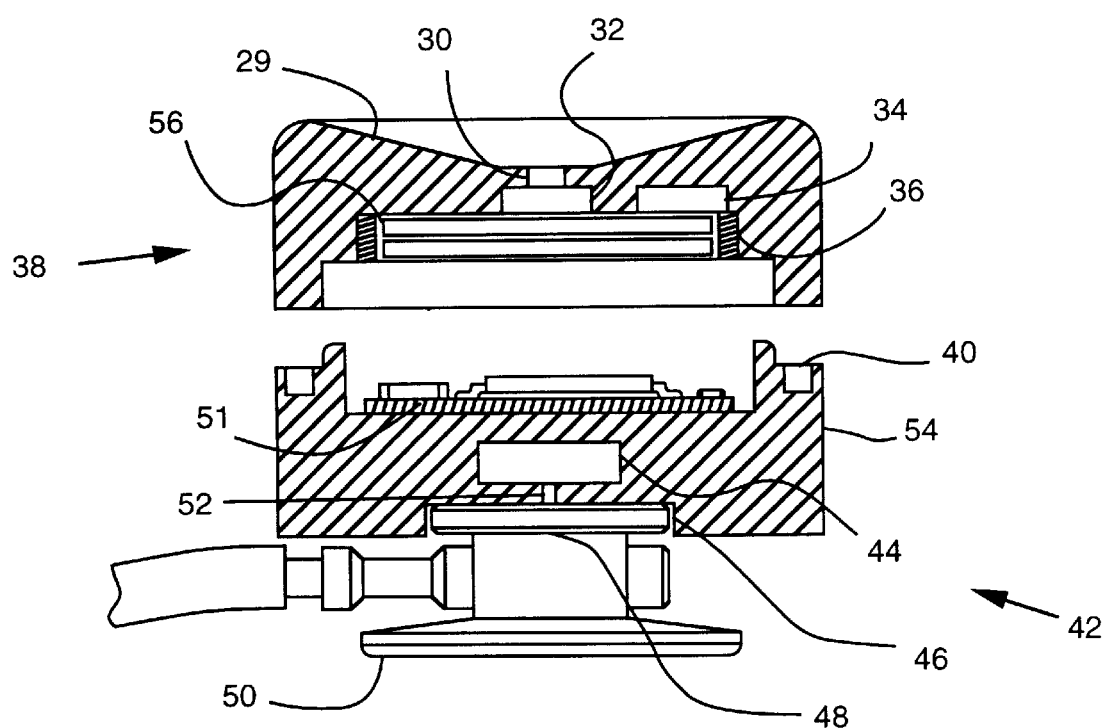
FIG. 2 is cross-sectional view of the basic noise-canceling stethoscope system.

A cross-sectional view of the dual channel embodiment of the device of FIG. 1d is depicted in FIG. 2. The body of the device is shown to have two separable pieces 38 and 42 for ease of access to the batteries 56 and electronics 51. Electrical insulators 36 are provided between the device body and the batteries 56. When placed together to form a single module, a seal is formed by an o-ring in seat 40. The acoustic horn 29 of the device is placed in contact with the anatomy and conducts sounds through coupling aperture 30 to a first pressure sensitive transducer 30. An auxiliary, noise sensing pressure transducer 34 is in proximity to signal transducer 34. The outputs of both transducers 32 and 34 are electrically connected to the electronics 51. The amplified anatomy sounds are output from electronics 51 to speaker 44. A small coupling aperture 52 is provided for delivery of the sound to the bell 48 of a conventional stethoscope 50. A recessed seat 46 allows easy coupling of the stethoscope bell 48 with the device 54.

Figure 3:
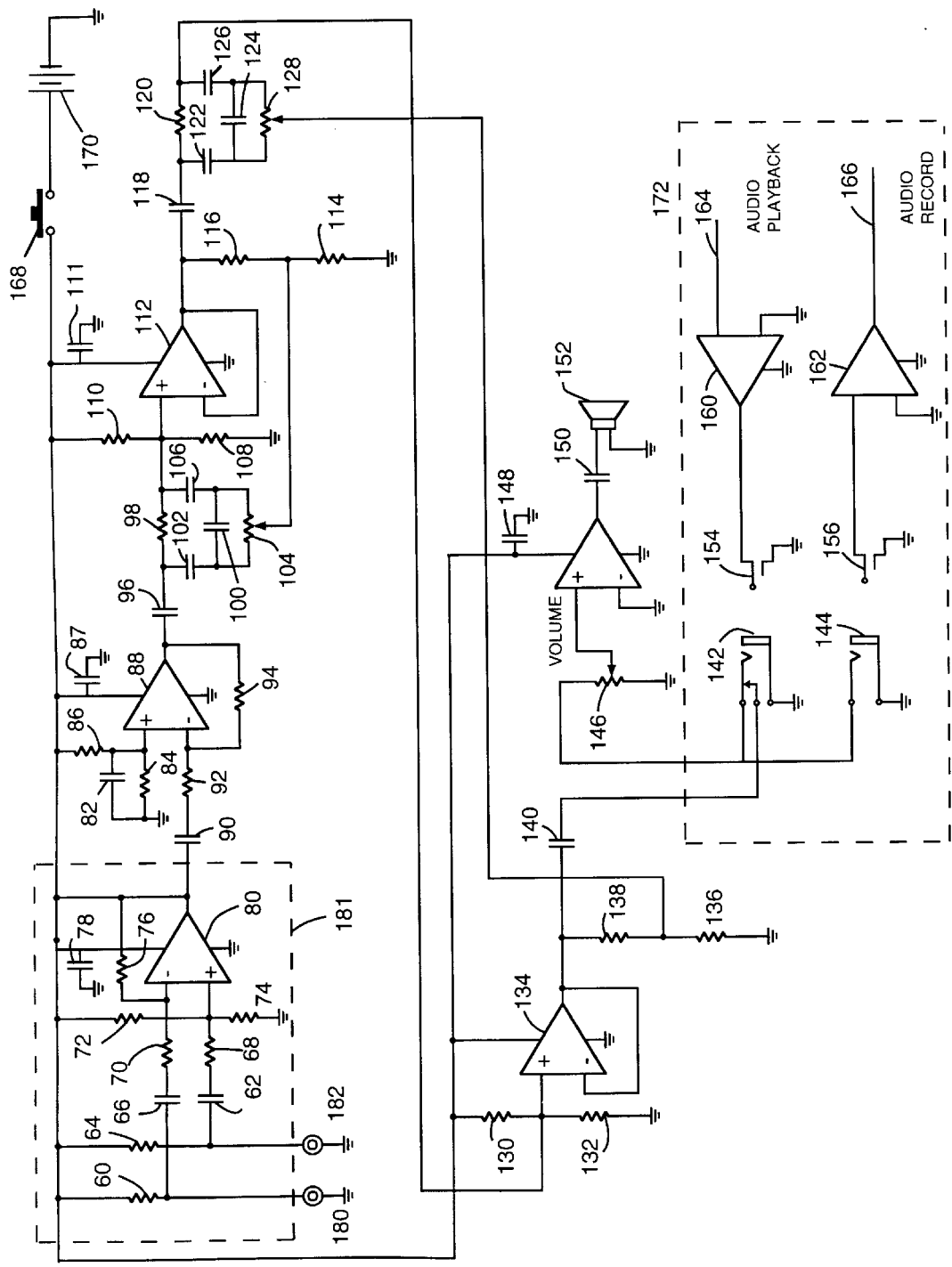
FIG. 3 is a schematic diagram for the basic noise-canceling stethoscope system circuitry (including recording and playback feature)

The electronic implementation of the noise-canceling process block 25 of FIG. 1d is given in FIG. 3. The primary pressure transducer 180 and auxiliary pressure transducer 182 can take the form of compact, sensitive electret condenser microphone cartridges such as the Panasonic P9963 device. These transducers are connected to the positive supply through current-limiting resistors 60 and 64, respectively. The small signal output of the devices is coupled through capacitors 66 and 62 to the differential amplifier. The differential amplifier comprises operational amplifier 80 and associated gain and bias resistors. Amplifier gain is established by resistors 70, and 76. Resistors 72 and 74 are bias resistors. The output of the differential amplifier is coupled through capacitor 90 to an inverting amplifier gain stage. The gain stage comprises operational amplifier 88 with gain establishing resistors 92 and 94, and a bias network consisting of resistors 84 and 86 with bypass capacitor 82. The amplified signal is coupled through capacitor 96 to two stages of active notch filtering. Because the output speaker 150 is in relative proximity to the input transducers 180 and 182, it is necessary to cancel any significant feedback between the acoustic output and the acoustic input of the stethoscope aid device. These stages of notch filtering do a good job of removing mechanical feedback resonances in the body of the device. Operational amplifiers 112 and 134 are shown used in a unity gain configuration. Operational amplifier 112 in concert with the network comprising capacitors 102, 106, and 100, and resistors 98, 116, and 114, with potentiometer 104 establish a first band-reject function that is tuned in frequency by adjustment of potentiometer 104. Likewise, operational amplifier 134 in concert with the network comprising capacitors 122, 124, and 126, and resistors 120, 136, and 138, with potentiometer 128 establish a second band-reject function that is tuned in frequency by adjustment of potentiometer 128. An optional audio recording and playback feature is provided by circuit 172. Upon insertion of jack 154 into receptacle 142, the signal path from the stethoscope aid device coupled through capacitor 140 is broken and a pre-recorded audio signal 164 is coupled through audio buffer amplifier 160 to output audio amplifier 148 and subsequently through capacitor 150 to speaker 150. For the purpose of auxiliary recording of the signal coupled through capacitor 140, jack 156 can be inserted into receptacle 144 to deliver the signal through audio buffer amplifier 162 as a record output 166.

Figure 4:
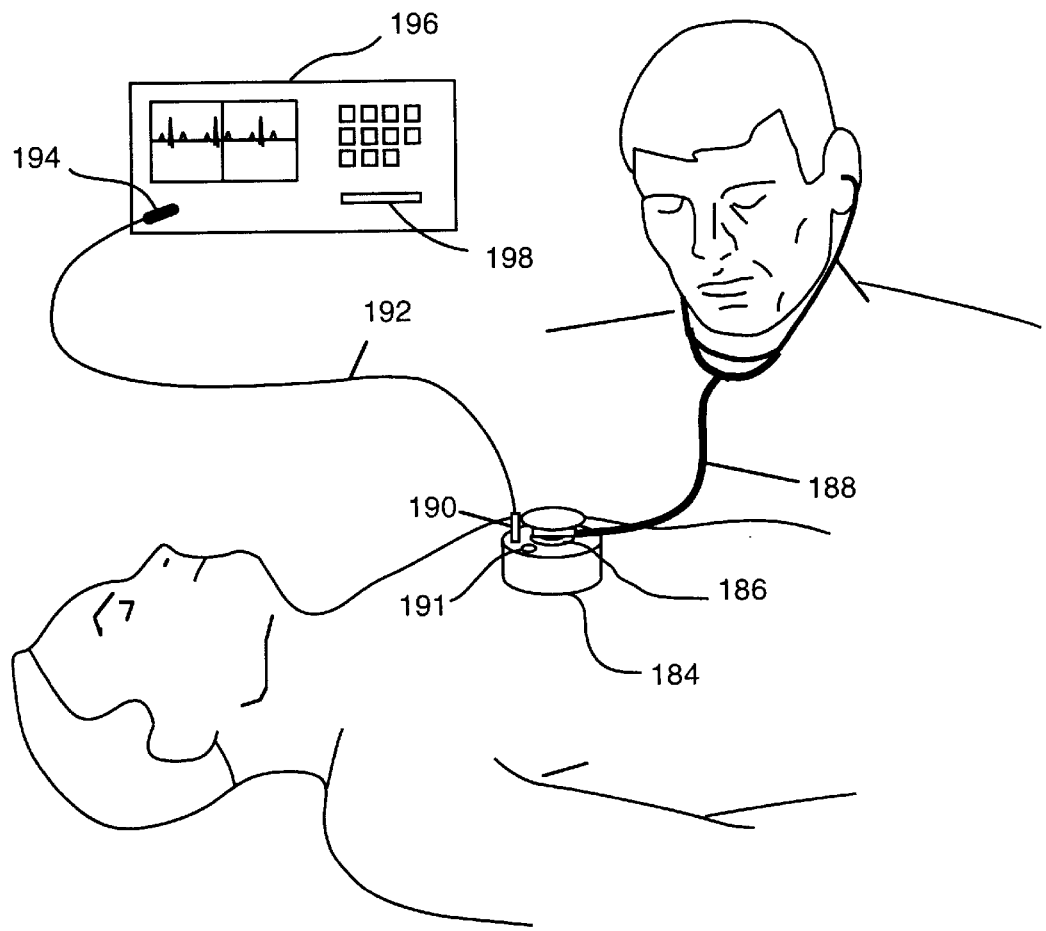
FIG. 4 is a pictorial diagram of the basic system using the recording output and playback capability.

FIG. 4 is a pictorial representation of this option in use. The trained ear of a medical professional can detect subtle variations in anatomy sounds, but the memory of such observations can blur over time. It would therefore be of value to record sounds for later assessment. Recording and playback device 196 can exploit as storage media, conventional magnetic tape or as depicted by slot 198, floppy disks or random access memory cards. This type of patient data could be stored with the patient's medical record. For example, if a cardiologist is tracking the condition of a particular patient he would be able to compare a present auscultation with one taken weeks or months earlier by simply inserting into device 196 the appropriate memory disk from the patients file. Pre-recorded anatomy sounds can be output through port 194 and connecting cable 192 to the stethoscope aid device 184 through playback jack assembly 190. A person can then listen to these sounds through a conventional stethoscope 188 at full fidelity when the stethoscope bell 186 is placed in contact with the device 184. In this mode the device 184 obviously does not have to be in contact with the patient. If cable 192 is connected through recording jack assembly 191, then anatomy sounds may be recorded by device 196 at the same time stethoscope 188 is used to listen to these sounds.

Figure 5A:
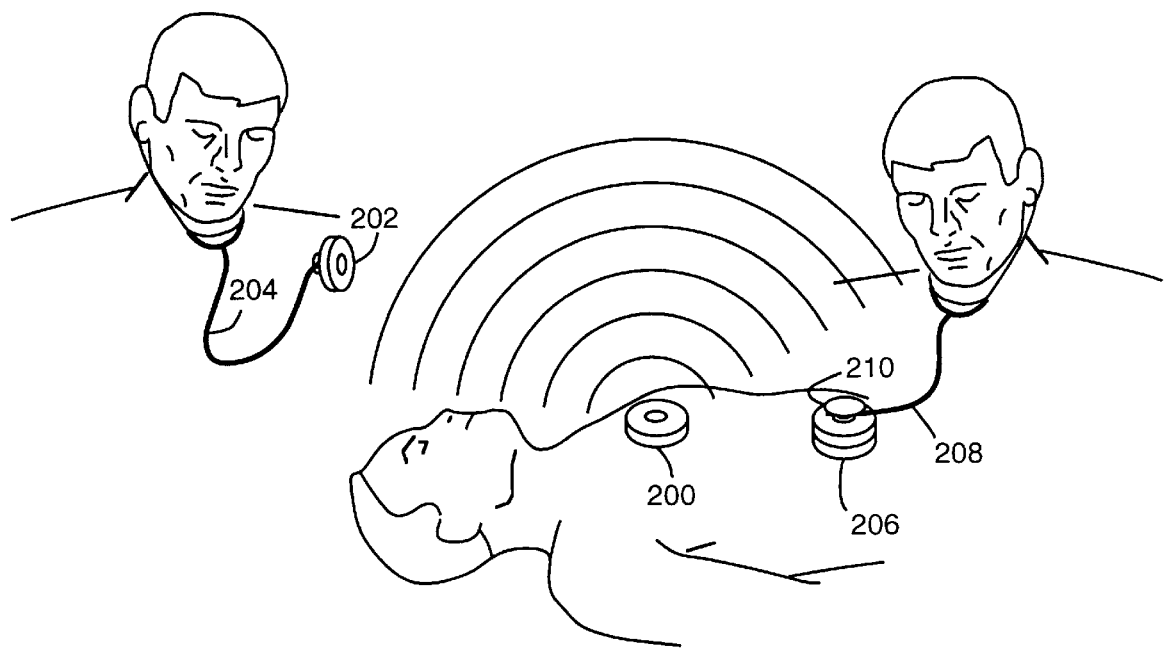
FIG. 5a is a pictorial diagram of the modular noise-canceling stethoscope.

FIG. 5a depicts a modular embodiment of the invention. In this embodiment, the sensing module (first module) can be separately located from the receiving module (second module) to allow greater versatility in using the instrument. Also, the first module is able to transmit to more than one receiving unit. Consequently, a plurality of receiving units and conventional stethoscopes can simultaneously monitor anatomical sounds. This would be quite valuable when more than one medical expert may be required to simultaneously monitor and diagnose the patient's condition quickly, when the device may be used in a teaching environment and many students might be required to monitor the patient simultaneously with the instructor, or where the anatomical sounds might be required to be recorded or transmitted over a telephone line by a suitable receiving unit. In addition, by simply re-engaging the two halves of the aid, the joined halves would act essentially as the single device idea of the first embodiment depicted in FIG. 1a. On the left of FIG. 5a, the device assembly is shown separated into two individual modules 200 and 202 that interlock to produce a single unit, shown on the right as device 206. Each of the modules 200 and 202 performs a distinct function such that when the two modules are physically separate but interacting they essentially perform the same overall function of the single unit of the first embodiment shown in FIG. 1a. This is shown on the right of FIG. 5a, where the modules operating while interlocked comprise device 206. The bell 210 of stethoscope 208 is placed in contact with the device as described earlier. In this second embodiment, module 200 contains the same acoustic collecting chamber, amplification electronics, and monitoring electronics. It has the additional capability of producing a radiated energy (either ultrasonic, radio frequency, or optical) carrier that is modulated with the anatomy sounds detected by the acoustic collection chamber and transmitted by a transmitting device (i.e., a resonant, high frequency ultrasonic transducer in the case of ultrasonics, an infrared diode in the case of optical energy, or a low power solid state radio frequency transmitter in the case of radio frequency energy). Any number of modulation schemes can be used that are well known in the prior art. These include amplitude, frequency and phase modulation formats in analog or digital form (and include spread spectrum schemes). The same differential amplification is contained in module 200. By modulating the carrier, the detected anatomy sounds are transmitted through some distance to the second module. The second module 202 contains a receiver to receive modulated energy from the first module 200. It also contains an amplifier and output speaker. When module 202 is mounted to the bell of the conventional stethoscope and module 200 is placed against the patient's body, anatomy sounds are heard through the stethoscope 204.

Figure 5B:
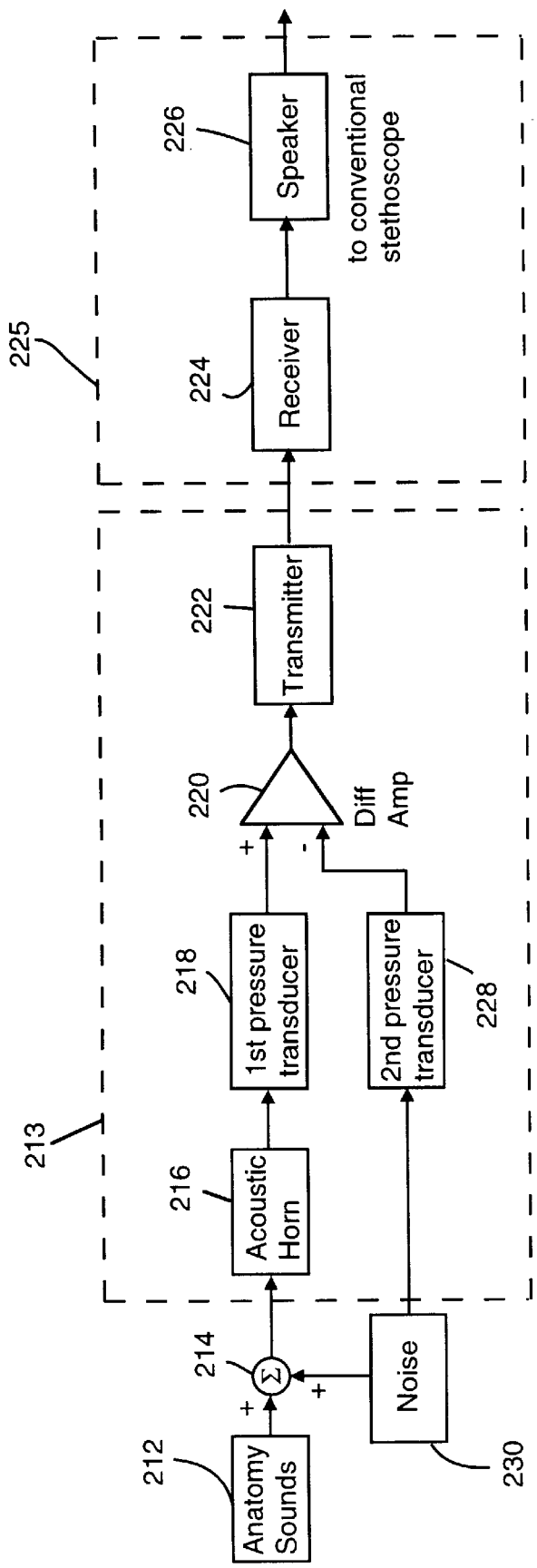
FIG. 5b is a functional block diagram of the modular noise-canceling stethoscope system.

FIG. 5b is the functional block diagram of the modular embodiment of the invention. Block 213 represents the functions contained in the first module and block 225 represents those functions contained in the second module. Anatomy sounds 212 and noise 230 are represented as joint inputs to the acoustic horn 216 by virtue of the summing junction 214. The first pressure transducer 218 receives this signal plus noise input, whereas, the second pressure transducer 228 in proximity to the first preferentially receives only the noise 230. The outputs of the respective transducers are input to a noise-canceling process as represented by differential amplifier 220. The output of the differential amplifier is relayed to the second module by transmitter 222. Within the second module 225, a receiver 224 detects and amplifies the signal in order to drive speaker 226. A conventional stethoscope receives the acoustic output from speaker 226. Any number of transmitter—receiver implementations are feasible that make use of different combinations of carrier energy type and modulation format; ultrasonic acoustic, and optical and radio frequency electromagnetic carriers with amplitude, phase or frequency modulation formats are possible.

Figure 6:
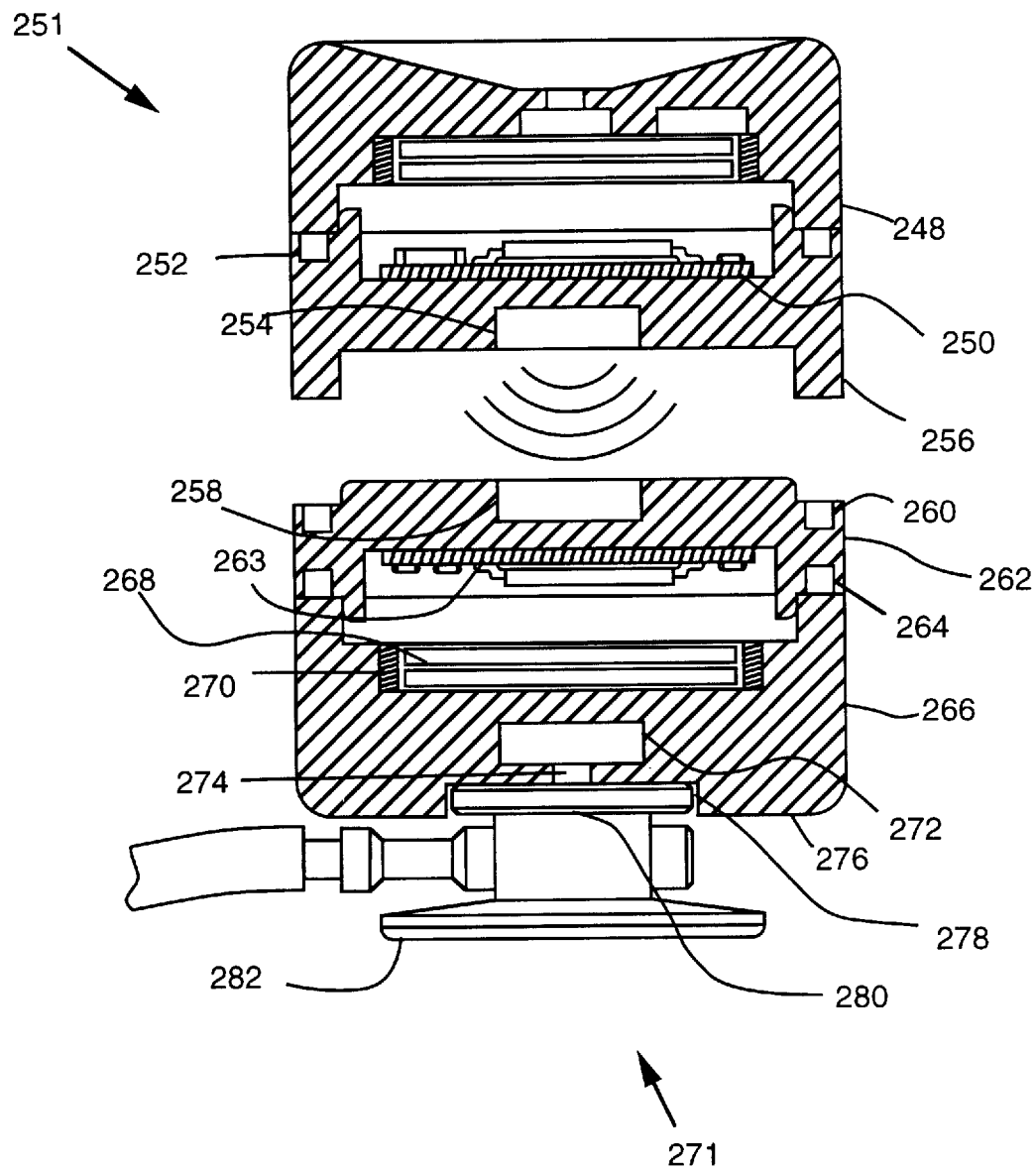
FIG. 6 is a cross-sectional diagram of the modular noise-canceling stethoscope system.

A cross-sectional view of the modular embodiment of the noise-canceling stethoscope aid that uses ultrasound is provided by FIG. 6. The first module 251 is shown separated from the second module 271. The first module 251 is further separable into two pieces 248 and 256. The piece 248 is the same as piece 38 of FIG. 2 containing the pressure sensing transducers and batteries (that in the present instance power first module 251). An o-ring seal 252 is provided for the engagement of pieces 248 and 256. The electronic circuitry 250 receives input from the transducers of piece 248 and outputs a modulated drive signal to a transmitting ultrasonic transducer 254. This signal is received by an ultrasonic transducer 258 in the second module 271 and fed to electronics 263 for output to speaker 274. Speaker sound is radiated through aperture 274 to the bell 280 of a conventional stethoscope 282. The second module 271 is shown to be separable into two pieces 262 and 276 for ease of access to batteries 268 that power the second module 271. Insulators 270 separate the batteries 268 from the body of the module and recess 278 is provided for contact of the device with a stethoscope bell.

Figure 7:
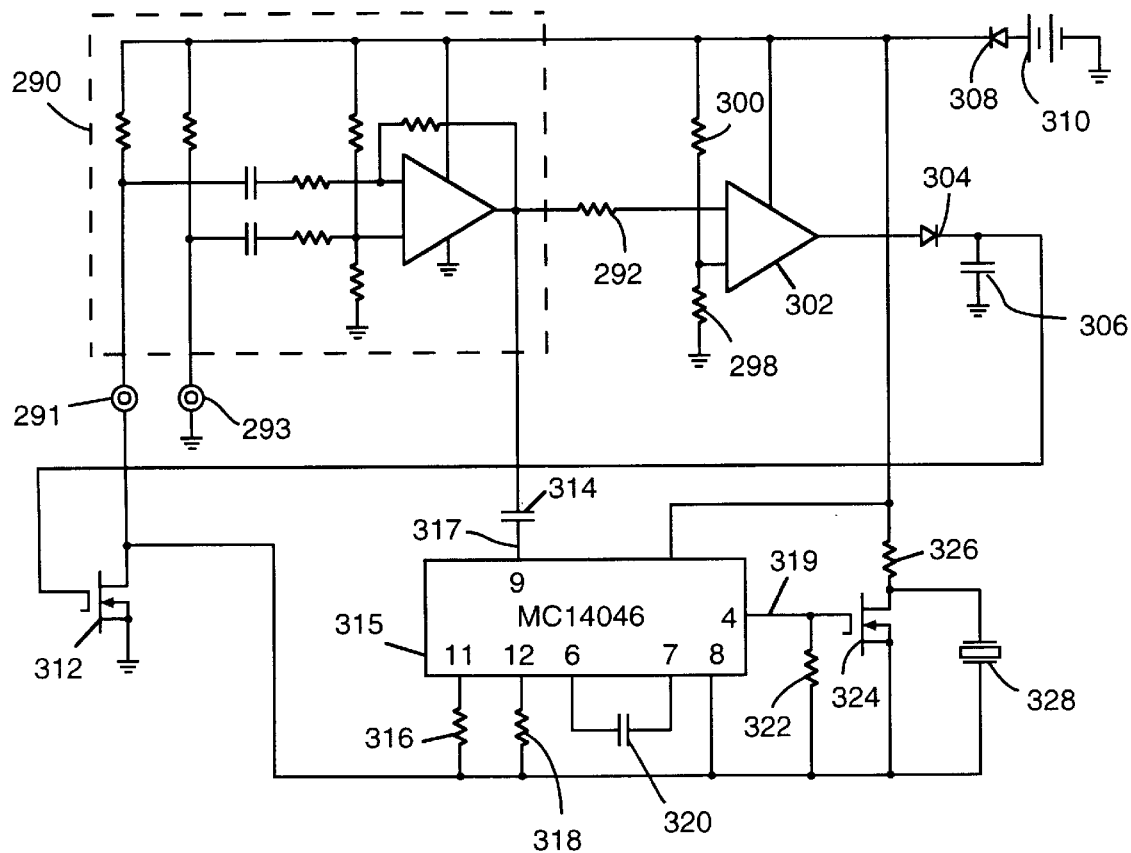
FIG. 7 is a schematic diagram of the modular noise-canceling stethoscope transmitter circuitry.

The electronic circuitry of the first module is shown in FIG. 7. Over and above the basic amplification function, the electronics also provides a novel means of automatically activating the device when the device is pressed against a patient's anatomy. An ultra low current monitoring circuit determines when the device comes in contact with the patient by detecting very low frequency pressure variations in the acoustic collection chamber characteristically produced when holding the device against the patient. These very low frequency pressure variations are in a spectral region well below the desired heart and breathing sounds that are to be amplified. The presence of these low frequency variations is used by the low-current monitoring circuitry to activate the rest of the electronics in the device. After initial activation using this means, the device stays activated as long as the pressure fluctuations in the acoustic collecting chamber are detected, that is, as long as the device continues to be held against the patient. When the device is removed from the anatomy, the characteristic low frequency fluctuations cease, causing the device to revert to an ultra-low current-consuming, standby mode. This feature not only provides for automatic activation of the device but also assures attainment of maximum battery life by automatic shutdown of most electronic functions when not in use. Another advantage is that in emergency situations the user does not have to remember to turn the unit on prior to use nor remember to shut it off afterwards. A low battery indicator annunciates the need to replace the internal battery when it is nearly exhausted.

The pressure transducers 291 and 293 provide input to the differential amplifier 290. This differential amplifier is of the same form as amplifier 181 shown in FIG. 3. As in the embodiment of FIG. 2, the first transducer 291 senses both anatomy sounds and noise and the second transducer 293 preferentially senses noise only. The output of the differential amplifier is applied to two inputs, that of a voltage comparator 302 and a voltage controlled oscillator (VCO). The module is powered by battery 310 through battery protection diode 308. The voltage comparator is used to conserve battery energy in the following manner. When the module is placed in contact with the body, a pressure transient will be sensed by transducer 291. Resistive divider network comprising resistors 298 and 300 establishes the comparator threshold voltage so that the signal due to this pressure transient will always be large enough to cause the output of the comparator 302 to go to the high state. This will allow capacitor 306 to become charged through diode 304 and field effect transistor (FET) switch 312 to switch on. Switch 312 then establishes a ground return connection for the transmitter circuitry that consumes the significant portion of the module power. The existence of anatomy sounds will cause the comparator output to remain high. Upon removal of the module from bodily contact, FET switch 312 will remain on for a duration determined by the discharge time constant associated with capacitor 306 and the FET input impedance (inasmuch as the comparator output impedance is not a discharge path because diode 304 is reverse biased). The output of the differential amplifier 290 is also coupled through capacitor 314 to the control input 317 of the voltage-controlled oscillator (VCO) contained in the CMOS phase locked loop chip 315. Resistors 316 and 318, and capacitor 320 set the free-running VCO frequency and its tuning range. The VCO output 319 drives FET 324 and impresses the frequency modulated (FM) signal voltage across the transmitting ultrasonic transducer 328.

Figure 8:
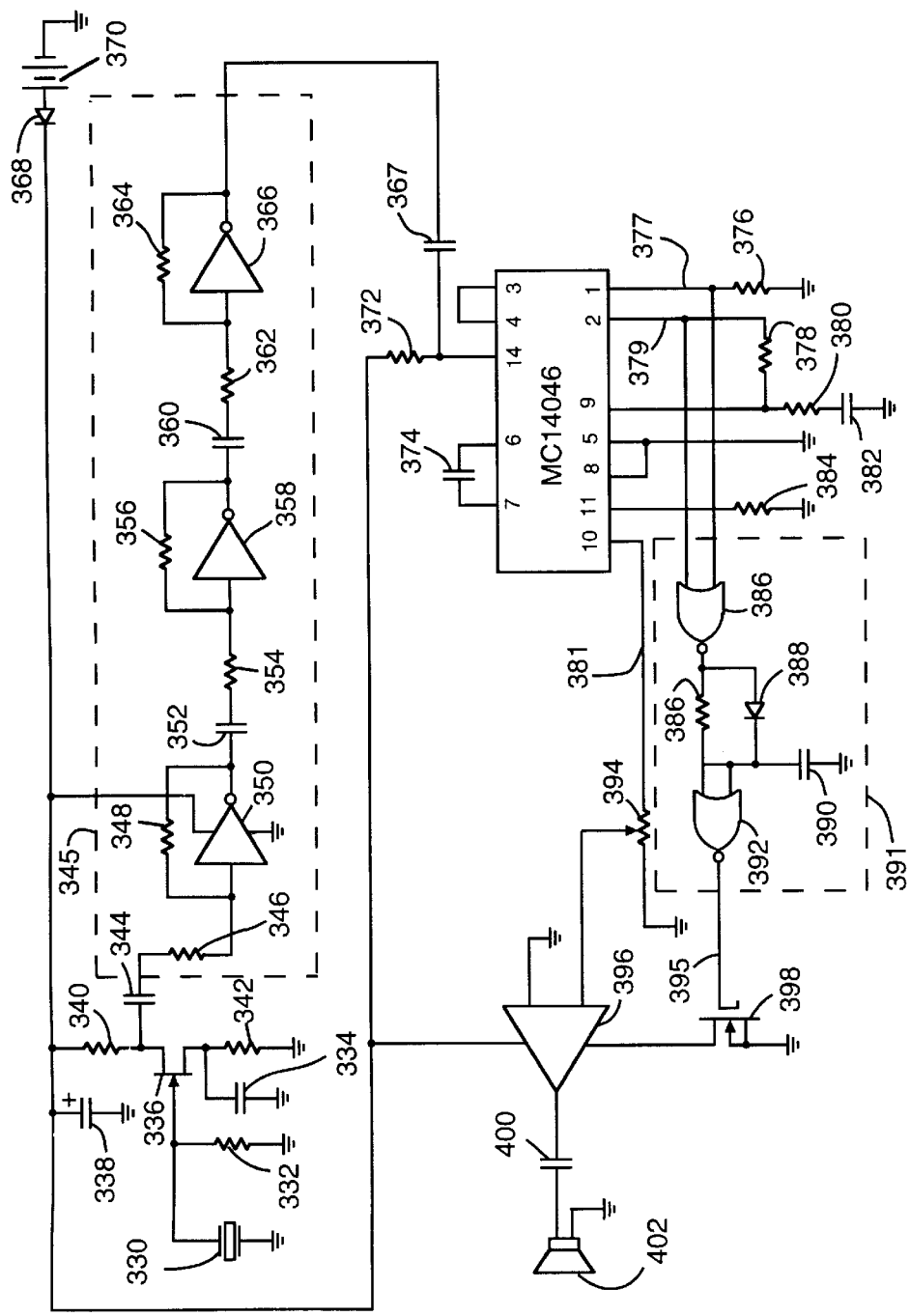
FIG. 8 is a schematic diagram of the modular noise-canceling stethoscope receiver circuitry.

FIG. 8 is a schematic diagram of the circuitry of the second module. Ultrasonic receiving transducer 330 provides an input signal to an FET amplifier comprising FET 336, bias resistors 340, 342, 332, and bypass capacitors 338 and 334. The amplifier output is input through capacitor 344 to a limiting amplifier chain 345 that uses three inverters 350, 358, and 366 of a hex inverter package such as the MC14049. Each inverter is operated in a linear amplifier mode by use of feedback resistors 348, 356, and 364, respectively. The linear gain of each stage is fixed by selection of the feedback resistors in combination with input resistors 346, 354, and 362. The signal is coupled between stages by capacitors 352 and 360. A wide dynamic range of signal strengths is accommodated by the receiver because of the limiting that occurs in the amplifier chain 345 at larger signal levels. Large signals will be received when the two modules are operating as one device or when they are separated, but in proximity. The amplified FM from amplifier chain 345 is demodulated using a phase-locked-loop (PLL). The amplifier chain output is coupled by capacitor 367 to the phase detector input of a PLL such as the CMOS MC14046 device 375. Capacitor 374 and resistor 384 set the VCO free-running frequency and tuning range. Resistors 378 and 380, and capacitor 382 form the PLL loop filter. The demodulated FM signal is a buffered output 381 that is coupled to audio amplifier 396 through a volume control variable resistor 394. Pulsed lock detection signal 377 and the PLL exclusive-OR phase detector output 379 are input to a lock detection circuit 381 that provides a constant level lock signal 395. When ultrasonic energy is not being received from the first module, conservation of battery 370 is achieved by disconnect of power to the relatively large current consuming audio output amplifier 396. The lock detection signal 395 is an indication that ultrasonic energy is being received from the first module and is therefore used to turn on the power to the audio amplifier 396 by FET switch 398. The audio signal is delivered from the audio amplifier 396 to the speaker 402 by capacitor 400.

FIG. 9a is a pictorial diagram of another embodiment of the invention wherein the second module of the device pictured in FIG. 5a is replaced with various forms of a remote receiving and relaying subsystem. A transmitting sensor subsystem 404 contains the same functions as the first module of FIG. 5a. It transmits anatomy sounds information on a modulated carrier to any of the receiving and relaying subsystems 407, 421 or 427, respectively. Receiving and relaying subsystem 407 comprises a receiver 408 that demodulates and amplifies the signal received from device 404, and a pair of noise-canceling headphones 406 that annunciate the received signal. Receiving and relaying subsystem 421 comprises a receiver 418 that demodulates and amplifies the signal received from device 404, and a recording device 420 that obtains the demodulated signal from receiver 418 by way of cable connection 416. Recording device 420 can record, analyze and playback anatomy sounds received from device 404. Conventional magnetic tape can be used as the storage media or as depicted by slot 422, floppy disks or random access memory cards can be implemented in device 420 as the storage media. Receiving and relaying subsystem 427 comprises a receiver 428 that demodulates and amplifies the signal received from device 404 and a signal analyzing device 424 that processes the received anatomy sounds for identification of medically significant features in the sound data. The signal analyzing device 424 can use autonomous processing, user-interactive workstation processing, or combination of both and would potentially archive data as well. Again, any number of transmitter—receiver implementations are feasible that use combinations of carrier energy type and modulation format; ultrasonic-acoustic, and optical and radio frequency electromagnetic carriers with amplitude, phase or frequency modulation formats are possible. Insert 409 in the upper right of FIG. 9a is a functional layout of any of the receivers 408, 418 or 428. Depicted is the receiving sensor 414 that may be a resonant ultrasonic device, an optical detector such as a photodiode or phototransistor, or an antenna. This sensor is electrically coupled to electronics 412. The electronics must perform the functions of signal amplification and demodulation. In the case of receiving and relaying subsystem 407 additional signal conditioning and processing may be desirable in order to enhance the signal prior to annunciation to the listener through the headphones. The output of the electronics 412 is then electrically coupled to the remainder of the receiving and relaying subsystem. A power supply 410 is shown that can be a battery supply contained in the receiver or can represent power delivered from a master power supply for the entire receiving and relaying subsystem.

A functional block diagram of the embodiment of FIG. 9a is given in FIG. 9b. Anatomy sounds 430 and associated noise 432 are processed in sensing and transmitting subsystem 443 for transmission of high fidelity anatomy sounds information to a receiving and relaying subsystem 447. The sensing and transmitting subsystem 443 performs the same functions as those of module 213 in FIG. 5b. Differential amplifier 444 subtracts the noise signal obtained from the second pressure transducer 440 from the composite anatomy sounds and noise signal obtained from the first pressure transducer 438. The anatomy sounds signal, now devoid of significant noise content, is output from differential amplifier 442 to transmitter 444. The receiving and relaying subsystem 447 comprises a receiver 446 and a number of subsequent hardware options. The received signal can be input to a recording and playback device 452, a signal analyzing device 454, headphones 450 or a signal enhancing device 448 prior to annunciation by headphones 449.

FIG. 10a is a pictorial diagram of a system embodiment that comprises a transmitting sensor subsystem 456 that contains the same functions as the first module of FIG. 5a, and a receiving and relaying subsystem further comprising a repeater 458 and a receiving and annunciating subsystem 459. The receiving and annunciating subsystem 459 is depicted as comprising a receiver 460 connected to headphones 462. Radio frequency communications systems often use repeaters to increase the range of communication. Such repeaters typically include a receiver, and a high power transmitter for retransmission of the received signal at much increased signal strength. Repeaters also incorporate the ability to receive control functions either on a subcarrier or a different frequency than that used for the signal information. Coded control information can turn on an idle repeater or adjust other parameters of its function. The repeaters used in the present invention transfer signal information from the low power sensing head of the invention to widely separated receiving devices and achieve transfer of this information using different forms of carrier energy and modulation formats. FIG. 10b is a functional block diagram of the embodiment of FIG. 10a. Anatomy sounds 466 and noise 478 are inputs to the transmitting sensor subsystem 464. The transmitter of device 464 broadcasts the signal information to repeater 488 of receiving and relaying subsystem 483. Repeater 488 can implement a processor 482 for signal enhancement prior to delivery of the signal to transmitter 486. Transmitter 486 then broadcasts the enhanced signal to a remote receiving and annunciating subsystem comprising a second receiver 490 and audio annunciating device 492.

FIG. 11 is a pictorial diagram of a system embodiment that comprises a transmitting sensor subsystem 532 that contains the same functions as the first module of FIG. 5a, and a receiving and relaying subsystem further comprising a first and second repeater 534 and 548, respectively, and remote monitoring means 550. Device 532 transmits anatomy sounds information to a first repeater 534 that comprises a receiver with output connection 536 to electrical means 540 for transmitting the received signal over the electrical power mains by way of electrical outlet 538. Electrical means of transmission over power mains can be an inductive coupling of the modulated signal voltage at appropriate amplitude onto to the power mains at the point where outlet power is received to power the device 534. This technique is well understood in the prior and has found application to remote machinery and appliance control. The signal transmitted over the electrical power mains is picked up at another power outlet 542 on the same circuit as outlet 538 by electrical means 544 that operates in the same manner as electrical means 540. The signal picked up by electrical means 544 is conducted to a second repeater 548 for rebroadcast to remote monitoring means 550 that contains the same functions as module 225 of FIG. 5b and hence provides audio output to a conventional stethoscope 552. Monitoring means may also include signal analyzers, recording devices, headphones, or earphones. This embodiment of the invention would be particularly useful to doctors wishing to maintain periodic assessments of certain patients in a large hospital setting while making rounds. It would provide anesthesiologists a form of constant contact with a patient if they exit the operating room during a medical procedure.

FIG. 12 is a functional block diagram of the embodiment of FIG. 11 that comprises a transmitting sensor subsystem 554 that contains the same functions as the first module of FIG. 5a, and a receiving and relaying subsystem further comprising a first and second repeater 568 and 574, respectively, and remote monitoring means 594. The transmitting sensor subsystem 554 broadcasts by acoustic, optical, radio frequency or direct electrical connection means to the first repeater 568. Receiver 570 amplifies and demodulates and remodulates the signal for transmission by electrical means 572 over the power mains 573 to the second repeater 574. The receiver 576 in the second repeater 574 amplifies, demodulates and remodulates the signal for subsequent transmission by transmitter 580. Transmitter 580 broadcasts the signal by acoustic, optical or radio frequency means to remote monitoring means 594 that comprises a receiver 582 connected to any of a number of devices such as a signal analyzing device 590, a recording and playback device 588, an audio annunciating device such as headphones 586 or a combination of a signal enhancing processor 584 and an audio annunciating device 592.

A further enhancement to the systems depicted in FIGS. 10a and 11 comprises the additional feature of a remote control function. A portable remote control unit can be implemented either as separate handheld device, much like a television control, or as part of the final annunciating equipment (device in contact with the stethoscope, recorder, or analyzer). This remote control device communicates with the repeater closest to the annunciating equipment in the case of multiple repeaters. The repeater relays this control information so as to turn the system on and off or adjust operational parameters of the system such as volume or noise quieting. Such a control system can be two-way, providing the user with status information regarding the system itself.

The full fidelity of a conventional stethoscope can be achieved in a system of the type shown in FIG. 9 or 10 by electronically incorporating the linear and nonlinear filter characteristics of the conventional stethoscope. A corresponding transfer function (pole-zero) model of a conventional stethoscope is given by FIG. 13 in block diagram form. Because of disparate conduction paths for anatomy sounds 600 and conducted noise 610, correspondingly different coupling transfer functions 602 and 610 are shown. Summation junction 604 depicts the combining of these signals in a common path through the stethoscope sensing head 606. The sensing head output and radiated noise represented by 614 and 612 are both introduced into the tubing piece as denoted by summing junction 616. The tubing has a linear transfer function 620 and a reverberant transfer function 618 shown in parallel combination at summing junction 622. The tubing output is then conducted through the binaural headpiece 624 and is coupled to the auditory canal 626. Measurement of these transfer functions and their implementation by electronics offers the potential to represent the acoustic behavior of a conventional stethoscope.

Software-based algorithms are pertinent to certain aspects of the presently disclosed invention. The noise-canceling process of FIG. 1b can be achieved by purely electronic means as discussed above in the form of difference amplification. An alternative is the use of software-based, processor-resident algorithms. Additionally, the embodiments of FIGS. 9 and 10 disclose processors that can make use of software-based filtering, recognition and enhancement algorithms.

Multichannel Noise Cancellation Techniques

The first stage in processing is the sensor fusion of information from both the primary sensor (or sensors) and the reference noise sensor (or sensors). Output from the primary sensor that senses both breathing and background acoustics, and the noise reference sensor that preferentially senses the acoustic background must be jointly processed to suppress background noise in the primary sensor channel. As can be seen in the spectrograms of lung sounds, there is considerable spectral overlap of breathing sounds and the acoustics of ambulance vehicles, for instance. Furthermore, both breathing sounds and the background noise are non-stationary to varying degrees. Hence, stochastic estimation techniques commonly applied in the speech processing realm recommend themselves. The categorization of such techniques into parametric (model-based) and nonparametric schemes is a convenient taxonomy for a discussion of these techniques.

An obvious advantage of nonparametric techniques is the reduced number of assumptions required regarding the nature of the spectra to be encountered. An example of the nonparametric approach to estimation is the adaptive filtering solution suggested by Widrow, et al. (1975). FIG. 14 shows the basic model of adaptive noise cancellation (Widrow and Stearns, 1985). With application to the problem at hand, s is the primary breathing sound signal 630 and $n_r$ is the reference noise signal 644. In this model, the reference noise $n_r$ (644) passes through some transformation H (646) (representing the conduction path from noise source to sensor) to form the primary noise signal $n_p$ (648). In general, this transformation can be nonlinear and time-variant. However, the success of adaptive noise cancellation depends upon the assumption that H is approximately linear. The composite signal p (634) is simply the sum of the primary breathing sound signal 630 and the primary noise signals 648. In order to enhance this composite signal, the reference noise is first processed by an adaptive filter $\hat{H}$ (642) resulting in an estimate y (640) of the primary noise. Finally, this noise estimate 640 is subtracted from the composite signal 634, yielding the enhanced output z (638). In this model, s and $n_r$ are modeled as uncorrelated random processes. In order for the output, z, to be a minimum-mean-squared-error (MMSE) estimate of the desired breathing sound signal, s, the adaptive filter must be varied so that the output noise power is minimized. Assuming, additionally, that s and $n_r$ are zero-mean, wide-sense stationary random processes, the output noise power can be written as $$E[(z-s)^2] = E[(z)^2] - E[(s)^2]$$

The signal power, $E[(s)^2]$, is unaffected by the adaptive filter. Therefore, the output noise is minimized by minimizing $E[(z)^2]$, the total output power, and it is easily shown that this equivalent to making y a MMSE estimate of $n_p$.

The adaptive filter, $\hat{H}$, can be implemented as a finite-impulse-response digital filter with time varying coefficients. Since the total output is a quadratic function of the filter coefficients, there exists a unique global minimum and many algorithms are adequate for approximating this minimum.

An example of a model-based approach to noise cancellation is the Estimate-Maximize (EM) algorithm of Feder, et al. (1987) that has been applied to the estimation of spectral parameters of speech in the presence of noise. In the case of speech the unknown parameters are linear predictive coding (LPC) coefficients. The algorithm iterates between Wiener filtering applied to the observations using the current spectral parameters of the signal (the E step), and updating the spectral parameters using the results of the Wiener filter (the M step). The LPC parameters are based on an autoregressive (AR) model of voiced speech; breathing sounds are more analogous to unvoiced speech, modeled as an autoregressive-moving average (ARMA) process. In the application of any parametric noise cancellation scheme some effort must be dedicated to the selection of appropriate spectral models for breathing sounds as discussed below in the section on filtering techniques.

Another approach to the separation of the desired signal from noise is the use of multiple primary sensors, with each such sensor receiving both desired signal and noise. The sensors may be spatially separated to insure that the noise input to each sensor is fully uncorrelated among sensors (in exploitation of the diffusivity of the noise field) and yet with signal inputs that remain highly correlated among sensors. A noise rejection filter can be formulated based upon the cross-covariances among these sensors. In the instance of very low initial signal-to-noise ratio, integration time will be required to achieve acceptable output. The multiple primary sensor approach may be couched in the formalism of multichannel detection theory that has seen considerable application in radar and sonar.

Filtering and Recognition Techniques

Filtering techniques include means for the identification and separation of features common to the desired signal and noise, respectively. The received composite signal must first be cast in a form from that a feature space can be constructed. For example, the signal may be transformed into a frequency domain representation such as the short term Fourier transform (STFT, spectrogram). The STFT provides a reasonable spectral representation for moderately stationary signals. A transform domain that has gained recent attention is that of time-frequency distributions that offer increased spectral resolution. Alternatively, the signal may be viewed in the time domain where features can be computed directly. Various features can be emphasized by the type of spectral estimation (or representation) used. Feature detection can be used to control an adaptive filter that emphasizes the energy in this feature or a filter can be constructed in the feature space for separation of desired signal from background.

Spectral Estimation. The observation record length limits on frequency resolution and the spectral leakage due to implicit windowing are particularly troublesome aspects of the FFT when analyzing short data records. Such short records are required given the inherently non-stationary character of much of the signal energy. In an attempt to alleviate these inherent limitations of the FFT approach, many alternative spectral estimation procedures have been proposed within the last decade. The apparent improvement in resolution provided by these techniques have fostered their popularity, even though classical FFT-based spectral estimation has been shown to often provide better performance at very low signal-to-noise ratios (S. L. Marple, Jr., 1989). Classical spectral estimation methods include the FFT periodogram and the Blackman-Tukey autocorrelation based technique. Parametric methods include the autoregressive (AR), autoregressive-moving average (ARMA), and Prony's method. Modern nonparametric methods include maximum likelihood spectral estimation (MLSE), Pisarenko harmonic decomposition, maximum entropy method (MEM) and the multiple signal classification (MUSIC) method.

Time-frequency distributions. Two-dimensional time-frequency representations of a signal are able to reveal features of highly non-stationary signals that are not apparent when using more conventional spectral methods. Important physical features such as instantaneous frequency (the limit of frequency resolution) and time delay are accessible.

Standard Fourier analysis allows the decomposition of a signal into various frequency components and establishes the relative intensity of each component. The energy spectrum does not relate when those frequencies occurred. If the signal spectrum is slowly varying, a separate Fourier transform may be performed on each of several successive quasi-stationary records of the signal to provide the short-time Fourier transform, or spectrogram. There exist signals whose spectral content is changing so rapidly that no practical short-time window is available over that the signal remains more or less stationary. Also, decreasing the time window to obtain temporal resolution for an event reduces the frequency resolution. One approach to the circumvention of this inherent tradeoff between time and frequency resolution is the definition of a joint function of time and frequency that will describe the energy density or intensity of a signal simultaneously in time and frequency. In recent years the Wigner and other distribution functions have been used for this purpose (B. Boashash and S. Abeysekera, 1986). This work has led to the recent development of the Wavelet Transform (WT). In contrast to the short-time Fourier transform that uses a single transform window, the WT uses short windows at high frequencies and long windows at low frequencies.

Connectionist techniques. A number of investigators have applied neural network paradigms to the problems of noise suppression in acoustic signals and feature extraction in radar (Malkoff and Cohen, 1990), sonar (Gorman and Sejnowski, 1986), and speech processing (Tamura and Waibel, 1988). In general, such networks require large amounts of labeled sample data and long training durations, but can achieve fairly robust filtering and recognition. The intriguing aspect of using a neural network is the implicit critical feature extraction afforded by diagnosis of connection weights.

REFERENCES

B. Boashash and S. Abeysekera (1986) "Two Dimensional Processing of Speech and ECG Signals using the Wigner-Ville Distribution," SPIE Vol. 697, *Applications of Digital Image Processing IX*, pp. 142–153.

C. R. Coler (1984) "In-Flight Testing of Automatic Speech Recognition Systems," *Speech Tech'84*, pp. 95–98.

P. Darlington, P. D. Wheeler, and G. A. Powell (1985) "Adaptive Noise Reduction in Aircraft Communication Systems," *ICASSP '85*, pp. 716–719.

M. Feder, A. V. Oppenheim, and E. Weinstein (1987) "Methods for Noise Cancellation based on the EM Algorithm," *ICASSP '87*, pp. 201–204.

R. Gorman and T. Sejnowski (1986) "Learned Classification of Sonar Targets Using a Massively-Parallel Network," *Proceedings of the Digital Signal Processing Workshop* (1986), sponsored by IEEE Acoustics, Speech, and Signal Processing Society.

D. B. Malkoff and L. Cohen (1990) "A Neural Network Approach to the Detection Problem using Joint Time-Frequency Distributions," *ICASSP '89*, pp. 2739–2742.

S. L. Marple, Jr. (1989) "A Tutorial Overview of Modern Spectral Estimation," Glasgow, Scotland, *ICASSP '89*, PP. 2152–2157.

S. Tamura and A. Waibel (1988) "Noise Reduction Using Connectionist Models," *ICASSP '89*, pp. 553–556.

B. Widrow, et al. (1975) "Adaptive Noise Canceling: Principles and Applications," *Proc. IEEE, Vol. 63*, pp. 1692–1716.

B. Widrow and S. D. Stearns (1985) *Adaptive Signal Processing*, Englewood Cliffs, N.J.: Prentice-Hall.

What is claimed is:

1. A noise-canceling system for the detection and amplification of anatomy sounds for presentation to a conventional stethoscope, said system comprising an assembly containing:

a) an acoustic sensing face placed in contact with a biological source of anatomy sounds for efficient coupling of sound into said noise-canceling system;

b) a first sound sensitive transducer receiving anatomy sounds coupled from said acoustic sensing face and noise sounds coupled from said acoustic sensing face as well as through the body of said assembly, said first sound sensitive transducer converting the combination of said anatomy sounds and said noise sounds into an electrical signal;

c) a second sound sensitive transducer contained in said assembly, said second sound sensitive transducer preferentially sensing said noise sounds and converting said noise sounds into an electrical signal;

d) a processing system receiving said electrical signals output from said first and second sound sensitive transducers, said processing system processing said electrical signals output from said first and second sound sensitive transducers so as to provide a noise-reduced output signal that contains energy due to said anatomy sounds, but is largely devoid of an energy contribution due to said noise sounds;

e) a sound transducer for output of signals from said processing system, said sound transducer providing an acoustic signal input to a conventional stethoscope;

f) means for delivering output of said processing system to said sound transducer;

g) a surface of shape complementary to the front side of the bell of a conventional stethoscope, said surface having at least one aperture therein for the transmission of acoustic energy from said sound transducer to said bell when said surface is mated with said bell, whereby, said noise-canceling system when used in concert with a stethoscope provides stethoscope output sound that has a signal-to-noise ratio improved over that available from an unaided conventional stethoscope.

2. A system as claimed in claim 1, wherein said means for delivering output of said processing system to said sound transducer is an electrical connection.

3. A system as claimed in claim 2, wherein said processing system provides an audio output for the purpose of recording sounds and an audio input for the replay of recorded sounds through said sound transducer.

4. A system as claimed in claim 2, wherein said processing system provides an audio output, said audio output connected to transmitting means for transmission of said audio to remote recording means.

5. A system as claimed in claim 1, including means of automatically activating said device when said device is pressed against a patient's anatomy, said means comprising low current drain monitoring circuitry, said monitoring circuitry detecting pressure variations at said acoustic sensing face characteristically produced by unavoidable relative motion between said system and patient's anatomy when holding said device against a patient's anatomy, said detection subsequently activating said device, said activation remaining as long as said low frequency pressure variations are detected.

6. A system as claimed in claim 1, wherein said assembly comprises two physically separable modules with said means for delivering output of said electronic circuitry to said sound transducer comprising a transmitter and receiver, the first of said modules comprising:

a) an acoustic sensing face placed in contact with the body for efficient coupling of sound into said noise-canceling system;

b) a first sound sensitive transducer receiving anatomy sounds coupled from said acoustic sensing face and noise sounds coupled from said acoustic sensing face as well as through the body of said first module, said first sound sensitive transducer converting the combination of said anatomy sounds and said noise sounds into an electrical signal;

c) a second sound sensitive transducer contained in said assembly, said second sound sensitive transducer preferentially sensing said noise sounds and converting said noise sounds into an electrical signal;

d) a processing system receiving said electrical signals output from said first and second sound sensitive transducers, said processing system processing said electrical signals output from said first and second sound sensitive transducers so as to provide a noise-reduced output signal that contains energy due to said anatomy sounds, but is largely devoid of an energy contribution due to said noise sounds;

e) transmitting means transmitting energy modulated with said noise-reduced output signal, and a second of such said modules comprising:

(a) receiving means receiving from said transmitting means energy modulated by said noise-reduced output signal and providing a reproduction of said noise-reduced output signal in electrical form;

(b) a sound transducer electrically connected to output of said receiving means providing acoustic output for sensing by a conventional stethoscope;

(c) said surface of shape complementary to the front side of said bell, said first module capable of transmitting to said second module when said first module and said second module are physically separated and also when said first module and said second module are in physical contact, said first module capable of transmitting to a plurality of said second modules for the purpose of allowing a plurality of listeners, each equipped with separate stethoscopes, to hear said acoustic output at the same time.

7. A system as claimed in claim 6, wherein said first module includes means of automatically activating said first module when said first module is pressed against a patient's anatomy, said means comprising low current drain monitoring circuitry, said monitoring circuitry detecting pressure variations at said acoustic sensing face characteristically produced by unavoidable relative motion between said first module and patient's anatomy when holding said first module against a patient's anatomy, said detection subsequently activating said first module, said activation remaining as long as said low frequency pressure variations are detected, and wherein said second module includes means of automatically activating said second module when said receiving means of said second module receives energy transmitted by said first module, said means of automatic activation comprising low current drain monitoring circuitry.

8. A system as claimed in claim 6, wherein said transmitting means comprises an electrical connection from the output of said processing system contained in said first module to the input of said receiving means contained in second said module.

9. A system as claimed in claim 6, wherein electronic circuitry of said second module has provision for an audio output for the purpose of recording sounds and an audio input for the replay of recorded sounds through said sound transducer.

10. A system as claimed in claim 6, wherein said transmitting means comprises an ultrasonic transmitter contained in said first module and said receiving means comprises an ultrasonic receiver contained in said second module.

11. A system as claimed in claim 6, wherein said transmitting means comprises an optical transmitter contained in said first module and said receiving means comprises an optical receiver contained in said second module.

12. A system as claimed in claim 6, wherein said transmitting means comprises a radio frequency transmitter contained in said first module and said receiving means comprises a radio frequency receiver contained in said second module.

13. A noise-canceling system for the detection, noise-suppressing amplification, and transmission of anatomy sounds to a remote receiving and relaying subsystem, said noise-canceling system comprising a transmitting sensor subsystem and a receiving and relaying subsystem, said transmitting sensor subsystem further comprising:

a) an acoustic sensing face placed in contact with the body for efficient coupling of sound into said noise-canceling system;

b) a first sound sensitive transducer receiving anatomy sounds coupled from said acoustic sensing face and noise sounds coupled from said acoustic sensing face as well as through the body of said transmitting sensor subsystem, said first sound sensitive transducer converting the combination of said anatomy sounds and said noise sounds into an electrical signal;

c) a second sound sensitive transducer contained in said transmitting sensor subsystem, said second sound sensitive transducer preferentially sensing said noise sounds and converting said noise sounds into an electrical signal;

d) a processing system receiving said electrical signals output from said first and second sound sensitive transducers, said processing system processing said electrical signals output from said first and second sound sensitive transducers so as to provide a noise-reduced output signal that contains energy due to said anatomy sounds, but is largely devoid of an energy contribution due to said noise sounds;

e) transmitting means, transmitting said noise-reduced output signal from said processing system to said receiving and relaying subsystem, said receiving and relaying system comprising the combination of a device selected from the group comprising receivers and repeaters, and a terminal-end device having a sound transducer housed in an assembly that exhibits a surface of shape complementary to the front side of the bell of a conventional stethoscope, said surface having at least one aperture therein for the transmission of acoustic energy from said sound transducer to said bell when said surface is mated with said bell.

14. A system as claimed in claim 13, wherein said transmitting means comprises an electrical connection from output of said processing system to input of said receiving and relaying subsystem.

15. A system as claimed in claim 13, wherein said transmitting means comprises an ultrasonic transmitter and said receiving and relaying subsystem comprises an ultrasonic receiver, receiving from said ultrasonic transmitter, ultrasonic energy modulated by said noise-reduced output signal and providing as output to said sound transducer, a reproduction of said noise-reduced output signal in electrical form.

16. A system as claimed in claim 13, wherein said transmitting means comprises an optical transmitter and said receiving and relaying subsystem comprises an optical receiver, receiving from said optical transmitter optical energy modulated by said noise-reduced output signal and providing as output to said sound transducer, a reproduction of said noise-reduced output signal in electrical form.

17. A system as claimed in claim 13, wherein said transmitting means comprises a radio frequency transmitter and said receiving and relaying subsystem comprises a radio frequency receiver, receiving from said radio frequency transmitter radio frequency energy modulated by said noise-reduced output signal and providing as output to said sound transducer, a reproduction of said noise-reduced output signal in electrical form.

18. A system as claimed in claim 13, wherein said transmitting means comprises an ultrasonic transmitter and said receiving and relaying subsystem comprises:

a) an ultrasonic receiver, receiving from said ultrasonic transmitter ultrasonic energy modulated by said noise-reduced output signal and providing as output, a reproduction of said noise-reduced output signal; and b) means for recording said reproduction.

19. A system as claimed in claim 13, wherein said transmitting means comprises an optical transmitter and said receiving and relaying subsystem comprises:

a) an optical receiver, receiving from said optical transmitter optical energy modulated by said noise-reduced output signal and providing as output, a reproduction of said noise-reduced output signal; and b) means for recording said reproduction.

20. A system as claimed in claim 13, wherein said transmitting means comprises a radio frequency transmitter and said receiving and relaying subsystem comprises:

a) a radio frequency receiver, receiving from said radio frequency transmitter radio frequency energy modulated by said noise-reduced output signal and providing as output, a reproduction of said noise-reduced output signal; and b) means for recording said reproduction.

21. A system as claimed in claim 13, wherein said transmitting means comprises a transmitter and said receiving and relaying subsystem comprises:

a) a first repeater, receiving from said transmitter, energy modulated by said noise-reduced output signal, said first repeater transmitting on electrical power mains a reproduction of said noise-reduced output signal, transmission over said power mains achieved by coupling of low power signals to said power mains;

b) a second repeater, receiving from said first repeater said reproduced, noise-reduced output signal over said power mains and transmitting by means other than said power mains, said reproduced, noise-reduced output signal; and c) final receiving means, receiving by means other than said power mains said reproduced, noise-reduced output signal from said second repeater, said final receiving means including said sound transducer, wherein a plurality of said second repeaters allows access to said reproduced, noise-reduced output signal by a plurality of users at the same time, at widely separated locations, and wherein a plurality of final receiving means allows a plurality of users to access said reproduced, noise-reduced output signal from a single said second repeater.

22. A system as claimed in claim 13, wherein said transmitting means comprises a transmitter and said receiving and relaying subsystem comprises:

a) a first repeater, receiving from said transmitter energy modulated by said noise-reduced output signal, said first repeater transmitting on electrical power mains a reproduction of said noise-reduced output signal and receiving on said power mains remote control information, transmission and reception over said power mains achieved by application of low power signals to said power mains, said remote control information causing the control of functioning of said first repeater;

b) a second repeater, receiving from said first repeater said reproduced, noise-reduced output signal over said power mains and transmitting to said first repeater said remote control information over said power mains, said second repeater receiving said remote control information and transmitting by means other than said power mains, said reproduced, noise-reduced output signal;

c) a remote controller that transmits said remote control information to said second repeater; and d) final receiving means, receiving said reproduced, noise-reduced output signal from said second repeater and transmitting said remote control information to said second repeater, said final receiving means including remote control input means and said sound transducer, wherein a plurality of said second repeaters allows access to said reproduced, noise-reduced output signal by a plurality of users at the same time, at widely separated locations, and wherein a plurality of final receiving means allows a plurality of users to access said reproduced, noise-reduced output signal from a single said second repeater.

23. A noise-canceling system for the detection and amplification of anatomy sounds for presentation to a conventional stethoscope, said system comprising an assembly containing:

a) an acoustic sensing face placed in contact with a biological source of anatomy sounds for efficient coupling of sound into said noise-canceling system;

b) a sound sensitive transducer receiving anatomy sounds coupled from said acoustic sensing face and noise sounds coupled from said acoustic sensing face as well as through the body of said assembly, said sound sensitive transducer converting the combination of said anatomy sounds and said noise sounds into an electrical signal;

c) a processing system receiving said electrical signal output from said sound sensitive transducer, said processing system processing said electrical signal output from said sound sensitive transducer so as to provide a noise-reduced output signal that contains energy due to said anatomy sounds, but is largely devoid of an energy contribution due to said noise sounds;

d) a sound transducer for conversion of said noise-reduced output signal to an acoustic signal for input to a conventional stethoscope;

e) means for delivering said noise-reduced output signal to said sound transducer;

f) a surface of shape complementary to the front side of the bell of a conventional stethoscope, said surface having at least one aperture therein for the transmission of acoustic energy from said sound transducer to said bell when said surface is mated with said bell, whereby, said noise-canceling system when used in concert with a stethoscope provides stethoscope output sound that has a signal-to-noise ratio improved over that available from an unaided conventional stethoscope.

24. A noise-canceling system for the detection and amplification of anatomy sounds for presentation to a conventional stethoscope, said system comprising an assembly that further comprises:

a) a plurality of sound sensitive transducers that receive anatomy sounds and noise sounds and convert said anatomy and noise sounds into electrical signals;

b) a processing system receiving said electrical signals output from said sound sensitive transducers and jointly processing said electrical signals so as to provide a noise-reduced output signal that contains energy due to said anatomy sounds, but is largely devoid of an energy contribution due to said noise sounds;

c) a sound transducer for acoustic transmission of said noise-reduced output signal to a stethoscope and;

f) a surface of shape complementary to the front side of the bell of a conventional stethoscope, said surface having at least one aperture therein for the transmission of acoustic energy from said sound transducer to said bell when said surface is mated with said bell.

25. A method of providing amplified anatomy sounds having an improved signal-to-noise ratio compared to the output of a conventional stethoscope, said method comprising:

a) collecting acoustic energy comprising anatomy and noise sound components by placing an acoustic sensing face in contact with a biological source of anatomy sounds;

b) conducting said acoustic energy from said acoustic sensing face to a first sound sensitive transducer, said first sound sensitive transducer converting said acoustic energy to an electrical signal;

c) detecting noise acoustic energy with a second sound sensitive transducer, said second sound sensitive transducer converting said noise acoustic energy to an electrical signal;

d) processing said output of said first and second sound sensitive transducers jointly so as to provide a noise-reduced output signal that contains energy due to said anatomy sounds, but is largely devoid of an energy contribution due to said noise sounds;

e) transmitting said noise-reduced output signal to a sound transducer for acoustic output of amplified anatomical sounds having improved signal-to-noise ratio; and f) housing said sound transducer in an assembly that has a surface of shape complementary to the front side of the bell of a conventional stethoscope, said surface having at least one aperture therein for the transmission of acoustic energy from said sound transducer to said bell when said surface is mated with said bell.

26. A method of providing amplified anatomy sounds having an improved signal-to-noise ratio compared to the output of a conventional stethoscope, said method comprising:

a) collecting acoustic energy comprising anatomy and noise sound components by placing an acoustic sensing face in contact with a biological source of anatomy sounds;

b) conducting said acoustic energy from said acoustic sensing face to a first sound sensitive transducer, said first sound sensitive transducer converting said acoustic energy to an electrical signal;

c) detecting noise acoustic energy with a second sound sensitive transducer, said second sound sensitive transducer converting said noise acoustic energy to an electrical signal;

d) processing said output of said first and second sound sensitive transducers jointly so as to provide a noise-reduced output signal that contains energy due to said anatomy sounds, but is largely devoid of an energy contribution due to said noise sounds;

e) transmitting said noise-reduced output signal to a relaying system;

f) receiving said noise-reduced output signal from said relaying system by final receiving means;

g) outputting, acoustically, said noise-reduced output signal from said final receiving means by a sound transducer; and h) housing said sound transducer in an assembly that has a surface of shape complementary to the front side of the bell of a conventional stethoscope, said surface having at least one aperture therein for the transmission of acoustic energy from said sound transducer to said bell when said surface is mated with said bell.

* * * * *